(12) United States Patent
El-Shall et al.

(10) Patent No.: US 9,768,355 B2
(45) Date of Patent: Sep. 19, 2017

(54) PRODUCTION OF GRAPHENE AND NANOPARTICLE CATALYSTS SUPPORTED ON GRAPHENE USING LASER RADIATION

(75) Inventors: M. Samy El-Shall, Richmond, VA (US); Victor Abdelsayed, Morgantown, WV (US); Saud I. Al-Resayes, Riyadh (SA); Zeid Abdullah M. Alothman, Riyadh (SA)

(73) Assignee: Virginia Commonwealth University, Richmond, VA (US)

( * ) Notice: Subject to any disclaimer, the term of this patent is extended or adjusted under 35 U.S.C. 154(b) by 805 days.

(21) Appl. No.: 13/514,671

(22) PCT Filed: Dec. 10, 2010

(86) PCT No.: PCT/US2010/059870
§ 371 (c)(1),
(2), (4) Date: Jun. 27, 2012

(87) PCT Pub. No.: WO2011/072213
PCT Pub. Date: Jun. 16, 2011

(65) Prior Publication Data
US 2012/0265122 A1    Oct. 18, 2012

Related U.S. Application Data

(60) Provisional application No. 61/285,271, filed on Dec. 10, 2009, provisional application No. 61/365,817, filed on Jul. 20, 2010.

(51) Int. Cl.
*C01B 31/02*     (2006.01)
*B01J 23/00*     (2006.01)
(Continued)

(52) U.S. Cl.
CPC ............ *H01L 33/343* (2013.01); *A61B 18/20* (2013.01); *A61K 41/0052* (2013.01);
(Continued)

(58) Field of Classification Search
CPC . B82Y 30/00; C01B 2204/24; C02F 2103/08; C02F 1/048
See application file for complete search history.

(56) References Cited

U.S. PATENT DOCUMENTS

| 2007/0131915 A1 | 6/2007 | Stankovich et al. |
| 2009/0068471 A1 | 3/2009 | Choi et al. |
| 2010/0266964 A1* | 10/2010 | Gilje .............................. 430/322 |

FOREIGN PATENT DOCUMENTS

WO    WO 2008-112639    9/2008

OTHER PUBLICATIONS

Abdelsayed et al. (Photothermal Deoxygenation of Graphite Oxide with Laser Excitation in Solution and Graphene-Aided Increase in Water Temperature, Sep. 10, 2010).*

(Continued)

*Primary Examiner* — Gary Jackson
*Assistant Examiner* — Scott T Luan
(74) *Attorney, Agent, or Firm* — Whitham, Curtis & Cook, P.C.

(57) ABSTRACT

Methods and apparatuses to produce graphene and nanoparticle catalysts supported on graphene without the use of reducing agents, and with the concomitant production of heat, are provided. The methods and apparatuses employ radiant energy to reduce (deoxygenate) graphite oxide (GO) to graphene, or to reduce a mixture of GO plus one or more metals to produce nanoparticle catalysts supported on graphene. Methods and systems to generate and utilize heat that is produced by irradiating GO, graphene and their metal and semiconductor nanocomposites with visible, infrared and/or ultraviolet radiation, e.g. using sunlight, lasers, etc. are also provided.

22 Claims, 19 Drawing Sheets

(51) Int. Cl.
| | |
|---|---|
| C02F 1/04 | (2006.01) |
| H01L 31/042 | (2014.01) |
| H01L 33/00 | (2010.01) |
| H01L 33/34 | (2010.01) |
| A61K 41/00 | (2006.01) |
| B82Y 30/00 | (2011.01) |
| H01L 29/66 | (2006.01) |
| H01L 29/786 | (2006.01) |
| B01J 37/16 | (2006.01) |
| B01J 37/34 | (2006.01) |
| B01J 21/18 | (2006.01) |
| B01J 23/89 | (2006.01) |
| B01J 35/00 | (2006.01) |
| C01B 3/40 | (2006.01) |
| B82Y 40/00 | (2011.01) |
| A61N 5/06 | (2006.01) |
| A61B 18/20 | (2006.01) |
| C01B 31/04 | (2006.01) |
| H01L 21/02 | (2006.01) |
| A61N 5/067 | (2006.01) |

(52) U.S. Cl.
CPC ............ *A61N 5/062* (2013.01); *B01J 21/185* (2013.01); *B01J 23/8913* (2013.01); *B01J 35/0013* (2013.01); *B01J 37/16* (2013.01); *B01J 37/349* (2013.01); *B82Y 30/00* (2013.01); *B82Y 40/00* (2013.01); *C01B 3/40* (2013.01); *C01B 31/0476* (2013.01); *H01L 29/66742* (2013.01); *H01L 29/78684* (2013.01); *H01L 33/0054* (2013.01); *A61N 2005/067* (2013.01); *C01B 2203/1041* (2013.01); *C01B 2203/1064* (2013.01); *C01B 2203/1082* (2013.01); *H01L 21/02527* (2013.01); *H01L 21/02628* (2013.01); *H01L 21/02656* (2013.01); *Y02P 20/52* (2015.11)

(56) References Cited

OTHER PUBLICATIONS

Nanowerk News ("The future of universal water: new study highlights water purification technology", Feb. 27, 2008).*

Xinxing et al., "A Functionalized Graphene Oxide-Iron Oxide Nanocomposite for Magnetically Targeted Drug Delivery, Photothermal Therapy, and Magnetic Resonance Imaging", Chem. Soc. Rev., 2012, 41, 782796.*

Xiang et al., "Graphene-based semiconductor photocatalysts", Nano Res. 2012, 5(3): 199-212.*

Zhou, Y, et al., "Microstructuring of Graphene Oxide Nanosheets Using Direct Laser Writing", Adv. Mater. (2010) 22, pp. 67-71.

Abdelsayed, V., et al., "Photothermal Deoxygenation of Graphite Oxide with Laser Excitation in Solution and Graphene-Aided Increase in Water Temperature", J. Phys. Chem. Lett. (2010) 1, pp. 2804-2809.

* cited by examiner

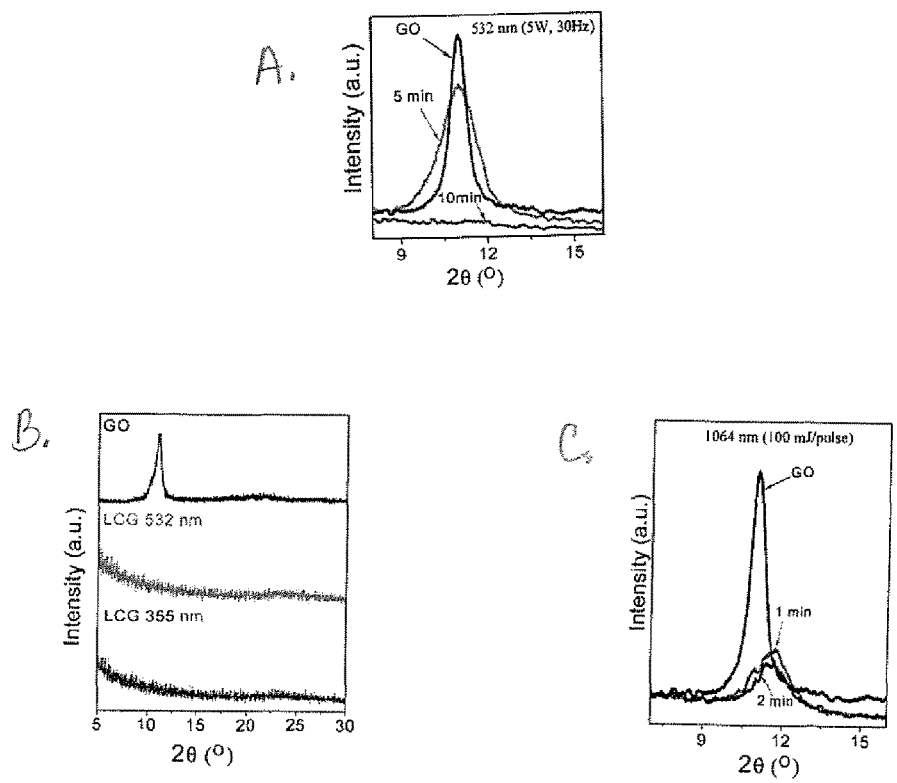
Figure 1A-C
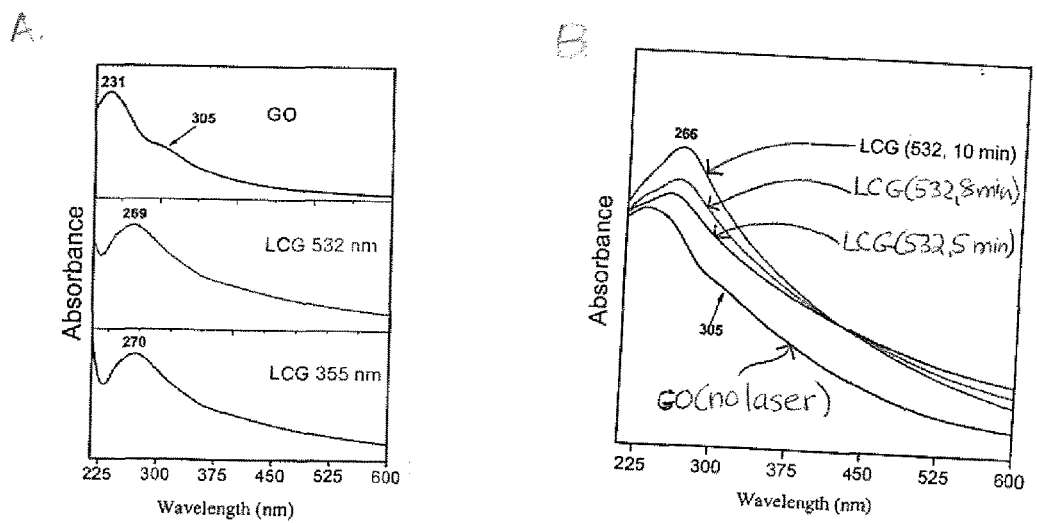
Figure 2 A and B

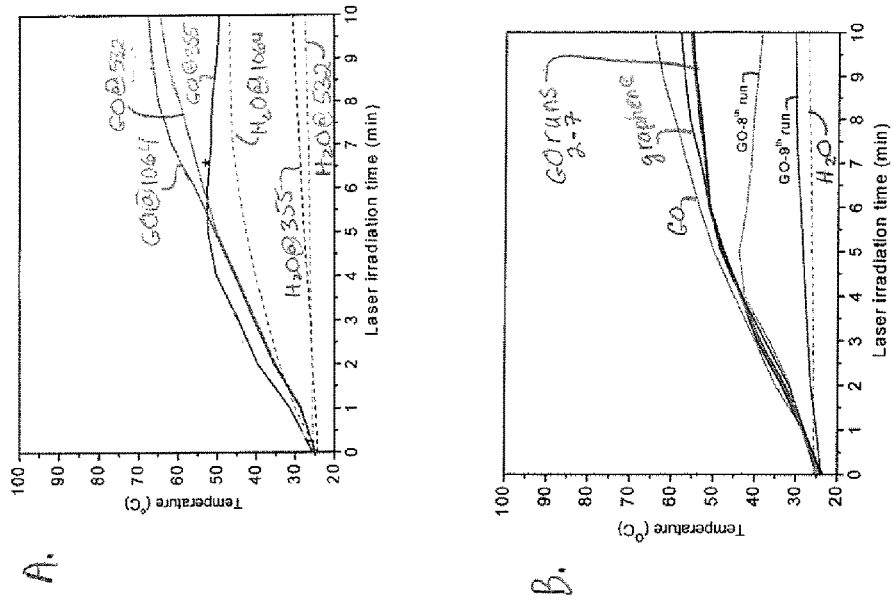
Figure 4 A and B
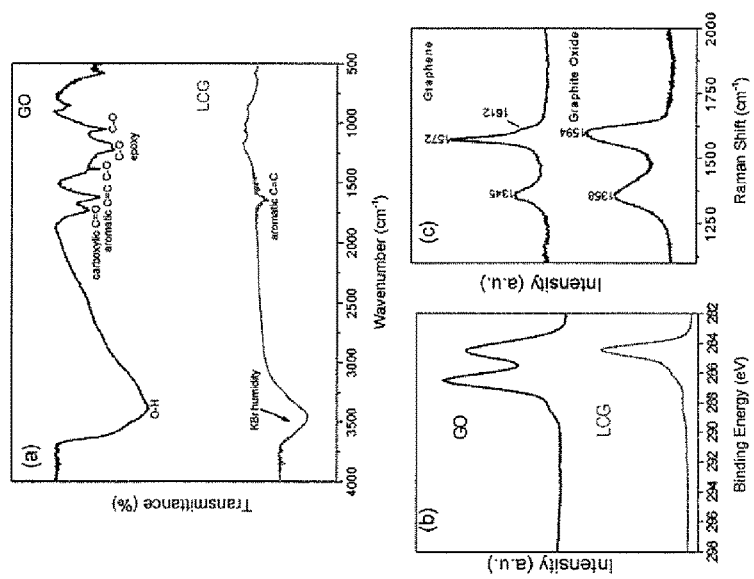
Figure 3 A-C

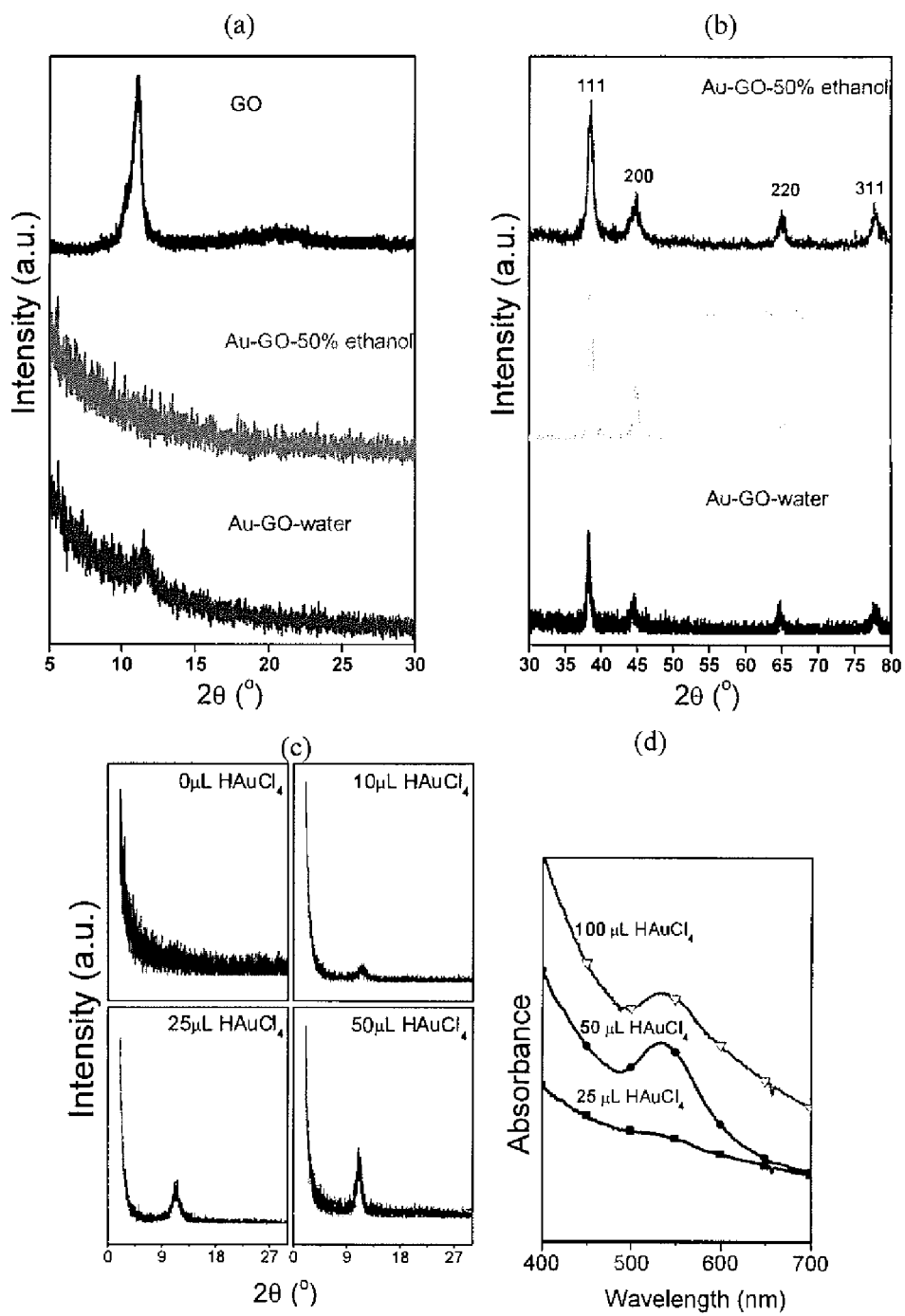
Figure 7 A-D

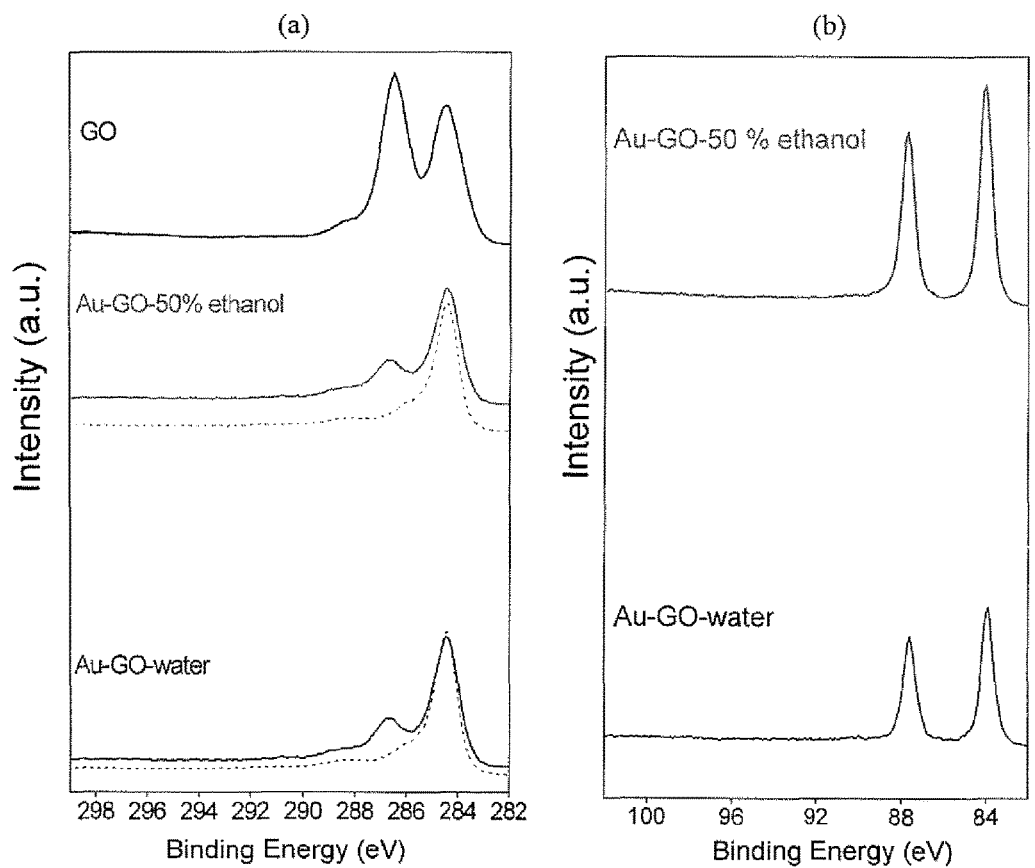
Figure 8 A and B

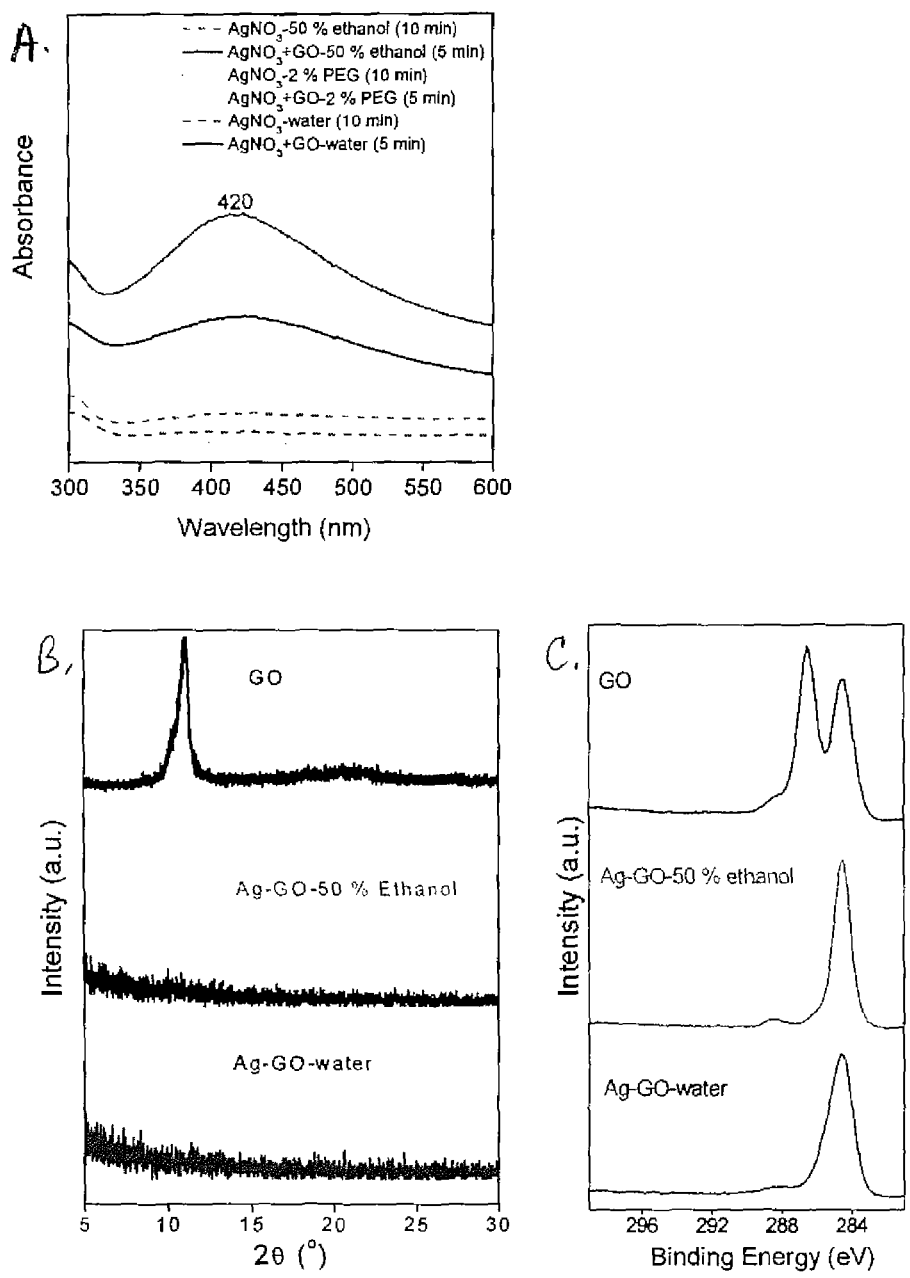
Figure 9 A-C

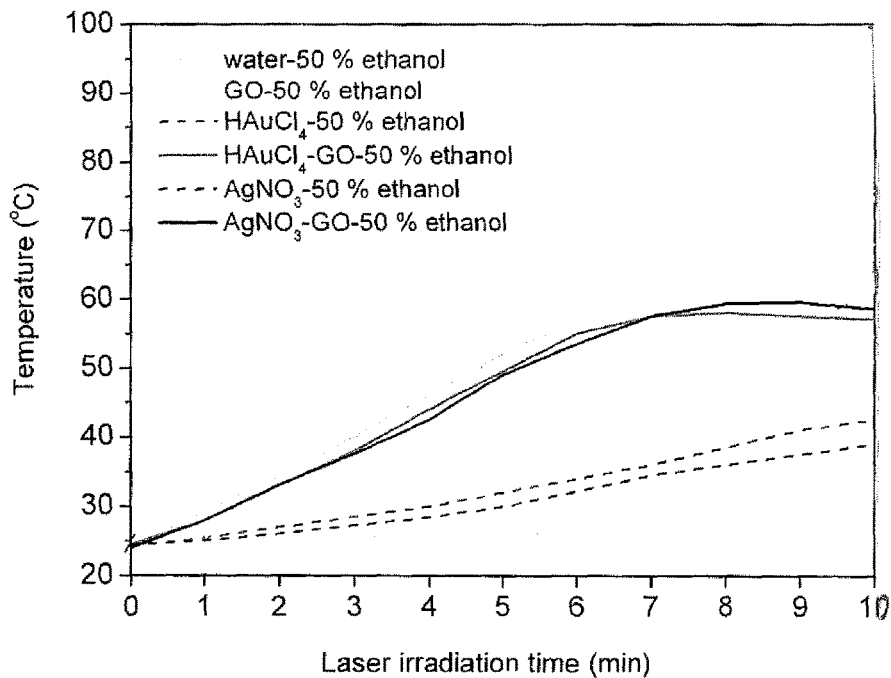
Figure 10
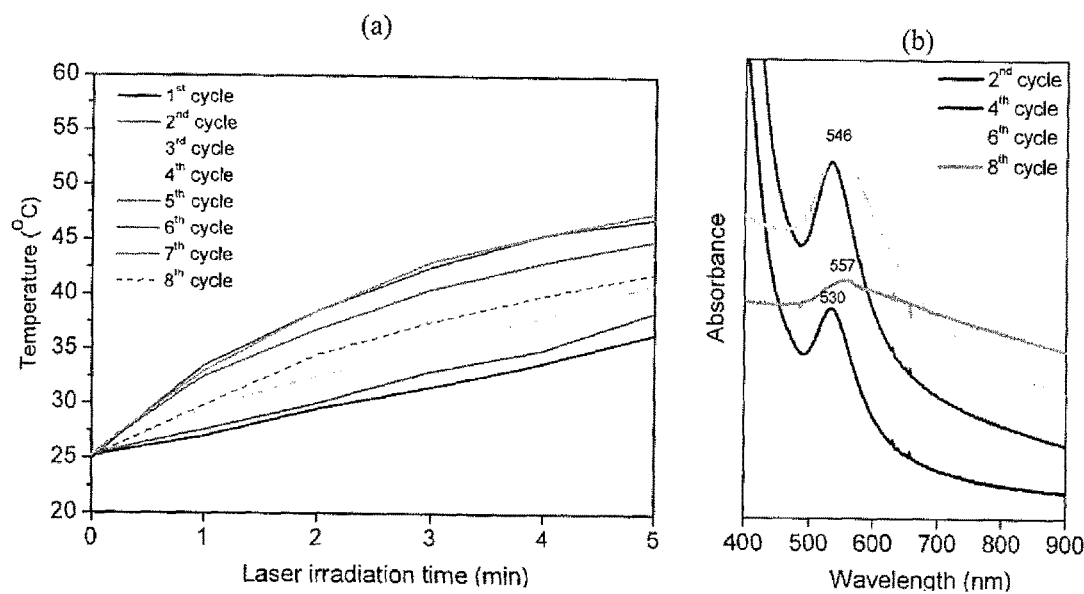
Figure 11 A and B

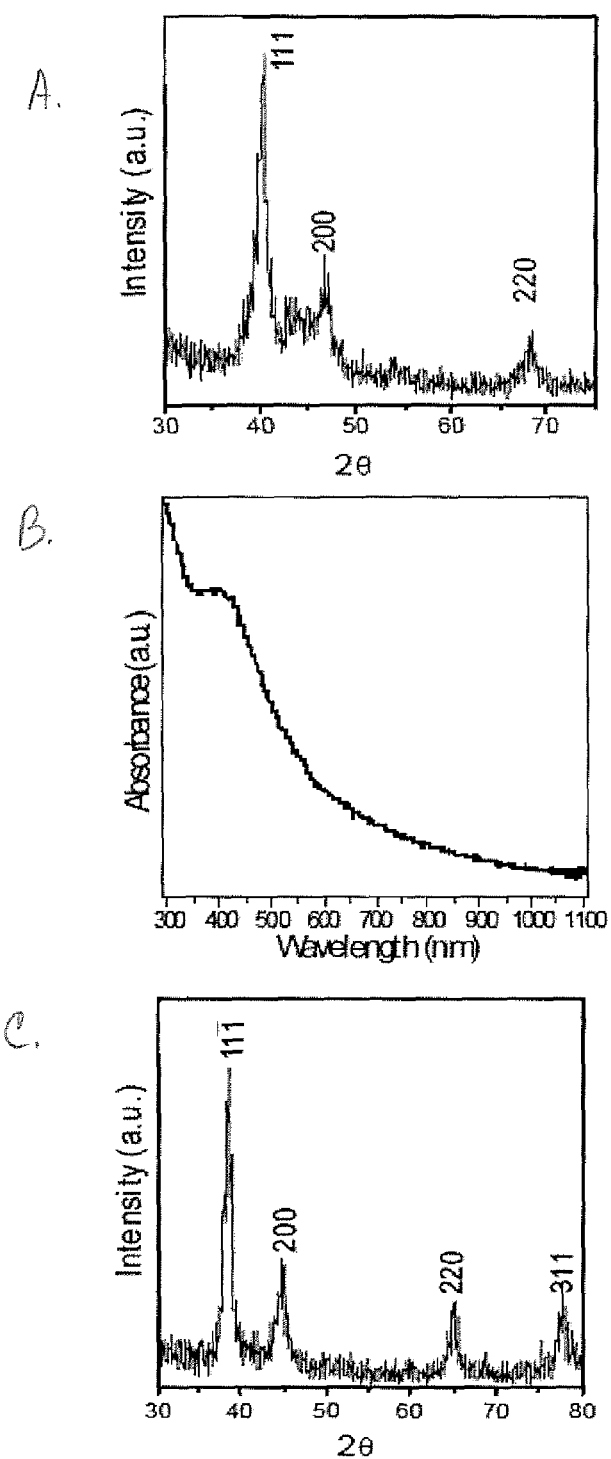
Figure 13 A-C

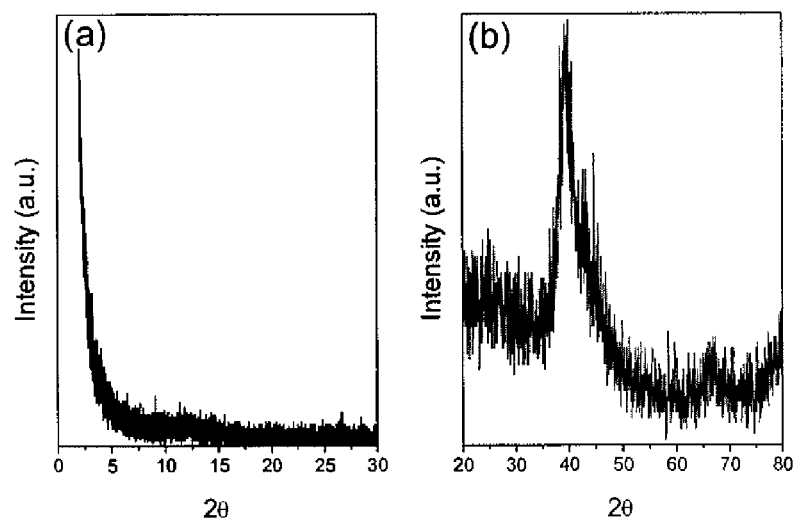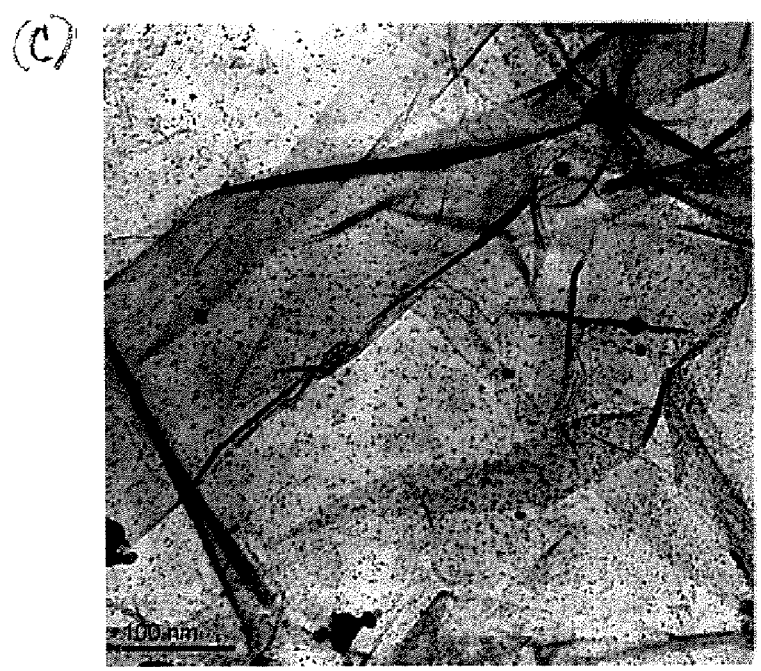
Figure 17A-C

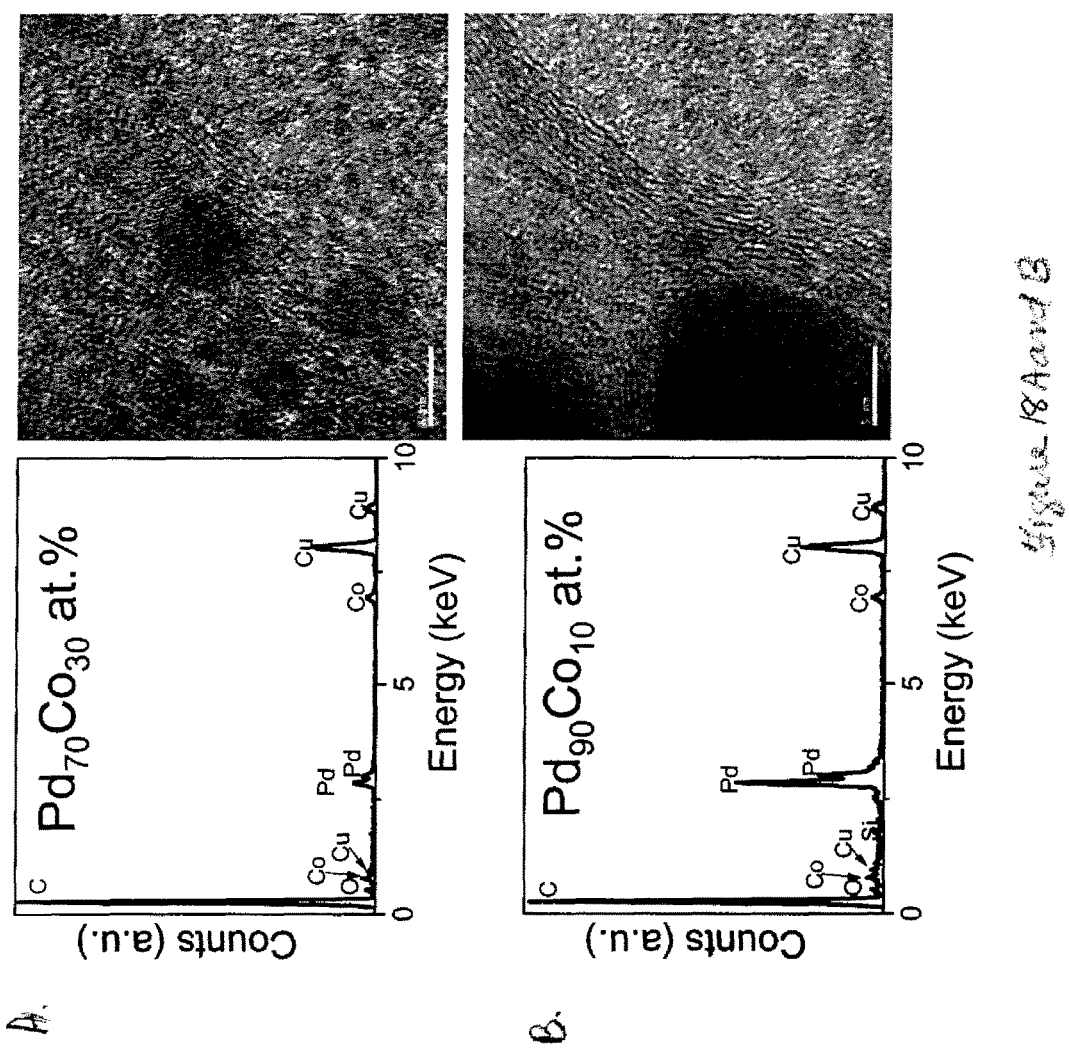
Figure 18A and B

US 9,768,355 B2

PRODUCTION OF GRAPHENE AND NANOPARTICLE CATALYSTS SUPPORTED ON GRAPHENE USING LASER RADIATION

CROSS-REFERENCE TO RELATED APPLICATIONS

This application is a 371 of International Application Number PCT/US2010/059870 filed Dec. 10, 2010, which claims benefit of U.S. provisional applications 61/285,271 filed Dec. 10, 2009 and 61/365,817 filed Jul. 20, 2010, all of which are incorporated herein by reference.

STATEMENT OF GOVERNMENT INTEREST

This invention was made with government support under contract number CHE-0414613 awarded by the National Science Foundation. The government has certain rights in the invention.

BACKGROUND OF THE INVENTION

Field of the Invention

The invention generally relates to methods and apparatuses to produce graphene and nanoparticle catalysts supported on graphene without the use of reducing agents. In particular, the invention provides methods and apparatuses which use ultraviolet (UV), visible (VIS) and/or infrared (IR) light to reduce (deoxygenate) graphite oxide (GO) to graphene, or to reduce a mixture of GO plus one or more metals ions to produce nanoparticle catalysts supported on graphene. The invention further provides methods and systems to generate and utilize heat that is produced by irradiating GO, graphene and their metal and semiconductor nanocomposites with UV, VIS, and/or IR radiation, e.g. using sunlight, lasers, etc.

Background of the Invention

The recent extensive interest in graphene associated with its unique hexagonal atomic layer structure and unusual properties, including the highest intrinsic carrier mobility at room temperature of all known materials, is motivated by the development of new composite materials for nanoelectronics, supercapacitors, batteries, photovoltaics, light-emitting diodes (LEDs) and related devices. Other properties of graphene such as the high thermal, chemical, and mechanical stability as well as high surface area also represent desirable characteristics as a 2-D catalyst support for metallic and bimetallic nanoparticles for a variety of applications in heterogeneous catalysis, sensors, hydrogen storage, and energy conversion.

Recent advances in the production of graphene sheets through the reduction of exfoliated graphite oxide (GO) have provided efficient approaches for the large scale production of chemically converted graphene (CCG) sheets. However, chemical reduction methods suffer from the difficulty of controlling the reduction process and residual contamination by the chemical reducing agents. This can cause detrimental effects, particularly for electronic applications of graphene. Therefore, there is a need for developing deoxygenation/reduction methods that do not rely on the use of chemicals or high temperatures. Recently, a flash reduction process was reported for the deoxygenation of GO films by photothermal heating of camera flash lights.[1,2] However, the method does not provide a solution process for the synthesis of individual graphene sheets because it was only applied to thin dry films of GO. Similarly, femtosecond laser pulses have been used for imprinting and patterning of 55 nm thick GO films, which resulted in partial reduction of the GO multilayer film with reduced depth of 35-25 nm, but the laser reduction process of individual GO sheets dispersed in water was not demonstrated.[3]

SUMMARY OF THE INVENTION

An embodiment of the invention provides methods of making graphene sheets and metallic catalysts supported on graphene sheets by exposing graphite oxide (GO) or GO plus one or more metal ions to UV, VIS, and/or IR radiation. In contrast to prior art methods, the methods of the invention do not require the use of other reducing agents to covert GO to graphene and thus contamination of the graphene by such agents and the generation of noxious by-products is eliminated. The technology provided herein is thus "green technology" i.e. the technology is environmentally friendly.

In another embodiment, of the invention, exposing GO, graphene, and metal and semiconductor nanocomposites of GO and graphene to UV, VIS, and/or IR radiant energy results in the highly efficient production of heat (photothermal energy conversion), and methods and apparatuses for the production of heat in this manner are provided. Advantageously, the materials used to generate heat in this manner can be regenerated and reused.

It is an object of this invention to provide a method of producing graphene, comprising the steps of 1) providing graphite oxide (GO); and 2) exposing said GO to a source of one or more of ultraviolet (UV), visible (VIS), or infrared (IR) radiant energy to produce graphene from said GO. In one embodiment, the GO provided in the providing step is in solution, and the solution may be an aqueous solution. In other embodiments, the solution comprises one or more organic solvents. In other embodiments, the GO provided in the providing step is solid graphite oxide. In some embodiments of the invention, the method is carried out in the absence of chemical reducing agents. In yet other embodiments, the GO provided in the providing step is mixed with at least one metal or metal alloy and the exposing step produces metal or metal alloy nanoparticles supported on the graphene. At least one of said at least one metals may be selected from the group consisting of Au, Ag, Pd. Co, Pd, Co, Au, Ag, Cu, Pt, Ni, Fe, Mn, Cr, V, Ti, Sc, Ce, Pr, Nd, Sm, Gd, Hom Er, Yb, Al, Ga, Sn, Pb, In, Mg, Ca, Sr, Na, K, Rb, and Cs.

In further embodiments, the GO provided in the providing step is mixed with at least one semiconductor material, and the exposing step produces semiconductor nanoparticles supported on the graphene. The at least one semiconductor material may be selected from the group consisting of silicon, titanium oxide and zinc oxide.

In yet other embodiments of the method, the providing step provides GO that is exfoliated.

The invention also provides a method of producing heat via photothermal energy conversion. The method comprises the step of exposing at least one photothermally active material to a source of one or more of ultraviolet (UV), visible (VIS), or infrared (IR) radiant energy, wherein the photothermally active material is selected from the group consisting of: graphite oxide (GO), partially reduced GO, graphene, a metal nanocomposite of GO, a metal nanocomposite of partially reduced GO, a metal nanocomposite of graphene, a semiconductor nanocomposite of GO, a semiconductor nanocomposite of partially reduced GO, and a semiconductor nanocomposite of graphene. In some embodiments, the at least one photothermally active material is dispersed in a liquid medium. In further embodiments, the source of one or more of ultraviolet (UV), visible (VIS), or infrared (IR) light energy is sunlight; in other embodiments, the source of one or more of ultraviolet (UV), visible (VIS), or infrared (IR) light energy is a laser.

The invention also provides an apparatus for producing heat via photothermal energy conversion. The apparatus comprises: 1) a container for containing at least one photothermally active material, the container permitting exposure of the at least one photothermally active material to a source of one or more of ultraviolet (UV), visible (VIS), or infrared (IR) light energy (the photothermally active material being selected from the group consisting of: graphite oxide (GO), partially reduced GO, graphene, a metal nanocomposite of GO, a metal nanocomposite of partially reduced GO, a metal nanocomposite of graphene, a semiconductor nanocomposite of GO, a semiconductor nanocomposite of partially reduced GO, and a semiconductor nanocomposite of graphene); 2) a container for containing a heatable medium; and 3) one or more conduits for transporting heated medium to location where heat is to be released from said heated medium. In some embodiments, the heatable medium is water. In other embodiments, the container for containing at least one photothermally active material and the container for containing a heatable medium are the same container.

The invention also provides an apparatus for desalinating sea water. The apparatus comprises 1) a container for containing at least one photothermally active material, the container permitting exposure of the at least one photothermally active material to a source of one or more of ultraviolet (UV), visible (VIS), or infrared (IR) light energy, and the photothermally active material being selected from the group consisting of: graphite oxide (GO), partially reduced GO, graphene, a metal nanocomposite of GO, a metal nanocomposite of partially reduced GO, a metal nanocomposite of graphene, a semiconductor nanocomposite of GO, a semiconductor nanocomposite of partially reduced GO, and a semiconductor nanocomposite of graphene; 2) a container for containing sea water; 3) a condenser for condensing water vapor; and 4) a receptacle for receiving condensed water vapor. In some embodiments, the container for containing at least one photothermally active material and the container for containing sea water are the same container.

The invention also provides a method for destroying unwanted cells or tissue in a subject in need thereof, comprising the steps of 1) placing at least one photothermally active material at or near said unwanted cells or tissue; and 2) exposing the at least one photothermally active material to a source of one or more of ultraviolet (UV), visible (VIS), or infrared (IR) radiant energy, the photothermally active material being selected from the group consisting of: graphite oxide (GO), partially reduced GO, graphene, a metal nanocomposite of GO, a metal nanocomposite of partially reduced GO, a metal nanocomposite of graphene, a semiconductor nanocomposite of GO, a semiconductor nanocomposite of partially reduced GO, and a semiconductor nanocomposite of graphene; Heat produced in the exposing step destroys said unwanted cells or tissue in said subject. In some embodiments, the unwanted cells or tissue are hyperproliferating cells or tissue.

The invention also provides a photovoltaic cell, comprising a transparent conducting layer, a photoabsorbing layer comprising at least one semiconductor nanocomposite of graphene; and a back electrode. In one embodiment, the transparent conducting layer comprises a graphene monolayer on a glass or polymer substrate; and in another embodiment, the back electrode comprises graphene. In some embodiments, the graphene is made by the methods of the invention.

In yet another embodiment, the invention provides a light-emitting-diode (LED), comprising a substrate, and a semiconductor nanocomposite of graphene associated with the substrate. The semiconductor nanocomposite of graphene is doped with impurities to create a p-n junction on the substrate. In some embodiments, the graphene is made by the methods of the invention.

BRIEF DESCRIPTION OF THE DRAWINGS

FIG. 1A-C. A, X-ray diffraction (XRD) of GO as a function of the 532 nm laser irradiation time (5 W, 30 Hz) at 0, 5, and 10 min irradiation times; B, XRD of GO, LCG after laser irradiation at 532 and 355 nm; C, XRD of GO following the 1064 nm laser irradiation for 1 and 2 min using 100 mJ/pulse, 30 Hz.

FIGS. 2A and B. A, UV-vis (ultraviolet-visible) spectra of GO and LCG dispersed in ethanol; B, UV-vis spectra showing the change of GO solution in water as a function of laser irradiation time (532 nm, 5 W, 30 Hz).

FIGS. 3A-C. A, Fourier transform-Infrared (FT-IR) spectra of graphite oxide (GO) and laser converted graphene (LCG); B, XPS C1s spectra of GO and LCG; C, Raman spectra of GO and graphene formed after laser irradiation of GO.

FIGS. 4A and B. A, Temperature changes during laser irradiation of graphite oxide solutions with the fundamental (1064 nm), $2^{nd}$ harmonic (532 nm), and 3rd harmonic (355 nm) of the neodymium-doped yttrium aluminium garnet (Nd/YAG) laser (5 W, 30 Hz). The * denotes bleaching the solution after 6 min with the 355 nm irradiation (5 W, 30 Hz). Dotted curves show the temperature changes of irradiating the same volume of pure water with the corresponding laser frequency (5 W, 30 Hz); B, Temperature changes during laser irradiation of graphite oxide solutions with the 2nd harmonic of the Nd/YAG laser (532 nm, 5 W, 30 Hz) after repeated irradiation cycles. The dashed curve shows the temperature change of irradiating the same volume of pure water with the 532 nm (5 W, 30 Hz). The results of cycles 2-7 were largely superimposable after about 4 minutes of radiation and are shown as one line.

FIG. 7A-D. A, XRD data of GO before and after the 532 nm laser irradiation (4 W, 30 Hz) for 10 minutes in different solvents as indicated. B, XRD data of Au nanoparticles incorporated within partially reduced GO. C, XRD data obtained after the 532 nm laser irradiation (4 W, 30 Hz) of GO in water containing different amounts of $HAuCl_4$ as indicated. D, Absorption spectra of GO solutions in water containing different amounts of $HAuCl_4$ as indicated after the 532 nm laser irradiation.

FIGS. 8A and B. A, XPS (C1S) spectra of GO and partially reduced GO containing Au nanoparticles prepared after 10 minutes laser irradiation (532 nm, 4 W, 30 Hz) of HAuCl$_4$-GO solutions in different solvents as indicated. B, XPS (Au 4f) spectra of Au nanoparticles incorporated in partially reduced GO prepared in different solvents as indicated.

FIG. 9A-C. A, Absorption spectra of AgNO$_3$-GO solutions in 50% ethanol-water, 2% PEG-water and pure water recorded after five minutes laser irradiation (532 nm, 4 W, 30 Hz). Dotted lines represent data of bank solutions containing the same amount of AgNO$_3$ but no GO after 10 minutes laser irradiation (532 nm, 4 W, 30 Hz). B, XRD data of GO before and after the 532 nm laser irradiation (4 W, 30 Hz) for five minutes in different solvents as indicated. C, XPS (C1S) spectra of GO and reduced GO containing Ag nanoparticles prepared after five minutes laser irradiation (532 nm, 4 W, 30 Hz) of AgNO$_3$-GO solutions in different solvents as indicated.

FIG. 10. Temperature changes during laser irradiation (532 nm, 4 W, 30 Hz) of GO solutions (3 mL solution, 2 mg GO/10 mL 50% ethanol-water) containing HAuCl$_4$ and AgNO$_3$. Comparisons with the HAuCl$_4$ and AgNO$_3$ solutions without GO under identical laser irradiation conditions are shown.

FIGS. 11A and B. A, Repeated laser irradiation (532 nm, 30 Hz, 2 W average power) cycles of 3 mL HAuCl$_4$+GO aqueous solution containing 10 μL HAuCl$_4$ and 0.6 mg GO. B, Absorption spectra of the HAuCl$_4$+GO solution recorded after different irradiation cycles using the 532 nm laser irradiation with an average laser power of 2 W.

FIG. 13A-C. A, XRD of Pd nanoparticles supported on graphene; B, UV-0V Is of Ag nanoparticles supported on graphene; c, XRD of Au nanoparticles supported on graphene. Pd, Ag and Au nanoparticles supported on graphene were prepared by the 532 nm laser irradiation in solution.

FIG. 17A-C. Laser synthesis of bimetallic PdCo nanoparticles supported on graphene. A, XRD data of reduced graphene oxide film containing PdCo nanoparticles showing the absence of the graphene oxide diffraction peak; B, XRD data of reduced graphene oxide film containing PdCo nanoparticles showing the diffraction peak due to PdCo bimetallic nanoparticles; C, TEM of bimetallic PdCo nanoparticles supported on graphene. bimetallic PdCo nanoparticles supported on graphene_

FIGS. 18A and B. EDS and TEM of laser synthesis of bimetallic PdCo nanoparticles supported on graphene. A, Atomic percent composition of the PdCo bimetallic nanoparticles supported on graphene showing a composition of 70% (at) Pd and 30% (at) Co.; B, Atomic percent composition of the PdCo bimetallic nanoparticles supported on graphene showing a composition of 90% (at) Pd and 10% (at) Co.

DETAILED DESCRIPTION

Figure 5:
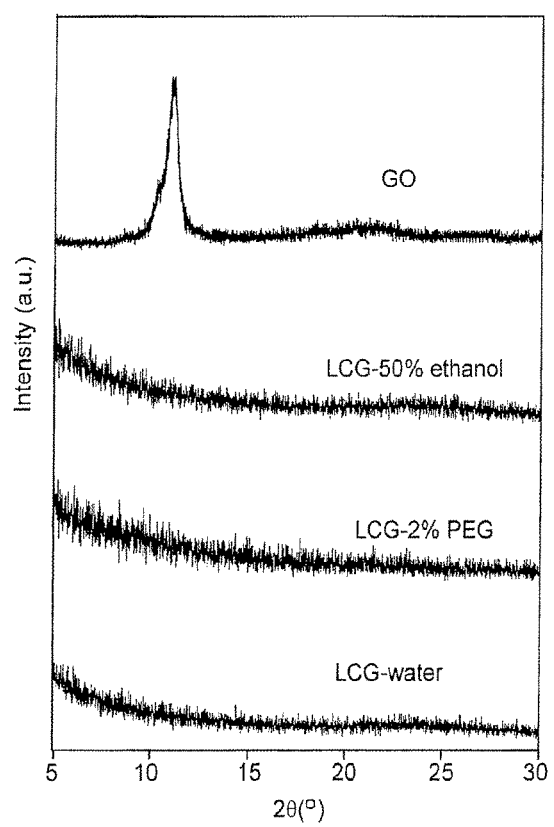
FIG. 5. XRD spectra of graphene oxide (GO) and laser-converted graphene (LCG) prepared by 532 nm laser irradiation (4 W, 30 Hz) of GO for 10 minutes in different solvents as indicated.

The invention provides advances in 1) the manufacture of graphene (using either GO in solution or solid GO); 2) the manufacture of metal catalysts supported on graphene; and 3) the generation of heat using reusable GO, graphene and metal or semiconductor nanocomposites thereof. Each of these embodiments has a myriad of applications and each is discussed in detail below.

The following definitions are provided:

By ultraviolet (UV) light we mean electromagnetic radiation with wavelength in the range of from about 10 to 400 nm. By "visible" (VIS) light, we mean electromagnetic radiation in the range of from about 390 nm to 750 nm. By "ultraviolet" light, we mean electromagnetic radiation in the range of from about 0.7 to about 300 micrometers (μm). For the sake of brevity, the ranges of electromagnetic radiation that are employed in the present invention may be collectively referred to herein as "light energy" or as "UV-VIS-IR energy" or "UV-VIS-IR light", and may encompass wavelengths from about 1 nm to about 500 μm, or from about 10 nm to about 300 μm, and usually from bout 100 nm to about 100 μm.

By "graphene" we mean sp$^2$-bonded carbon atoms that are densely packed in a one-atom-thick planar sheet. Graphene atoms form a honeycomb or "chicken-wire" atomic scale crystal lattice made of carbon atoms and their bonds. The crystalline or "flake" form of graphite consists of many graphene sheets stacked together.

"Graphite oxide" (formerly called graphitic oxide or graphitic acid) as used herein, refers to a compound of carbon, oxygen, and hydrogen in variable ratios, obtained by treating graphite with strong oxidizers. The maximally oxidized bulk product is a yellow solid with C:O ratio between 2.1 and 2.9, that retains the layer structure of graphite but with a much larger and irregular spacing. The structure and properties of graphite oxide are variable and depend on the particular synthesis method and degree of oxidation. It typically preserves the layer structure of the parent graphite, but the layers are buckled and the interlayer spacing is about two times larger (~7 Å) than that of graphite. Strictly speaking "oxide" is an incorrect but historically established name. Besides oxygen, epoxide groups (bridging oxygen atoms), and other functional groups experimentally found are in graphite oxide, e.g. carbonyl (=CO), hydroxyl (—OH), phenol groups, especially attached to the edges of each layer. There is evidence of "buckling" (deviation from planarity) of the layers, and the detailed structure is still not understood due to the strong disorder and irregular packing of the layers. Graphene oxide layers are about 1.1±0.2 nm thick.

By "exfoliated graphite oxide" we mean GO in which the layers have been separated.

By "oxidation" we mean the loss of electrons.

By "reduction" we mean the gain of electrons.

I. Production of Graphene

GO in Solution

In one embodiment of the invention, graphene is produced by irradiating, with "light" or "radiant" energy, GO in suspension or dispersed in a liquid medium without the use of any chemical reducing agent. Irradiation is carried out in a manner that results in reduction and hence deoxygenation of the GO, and the production of the characteristic $sp^2$-bonded carbon atoms densely packed in a one-atom-thick planar sheet.

Liquid media that can be used to disperse GO in a manner suitable for irradiation include but are not limited to: aqueous-based media such as water; aqueous solutions of water and alcohols such as ethanol (e.g. from about 10 to about 90% ETOH, or from about 20 to about 80%, or from about 30 to about 70%, or from about 40 to about 60%, and usually about 50% ETOH); solutions of polyethylene glycol (PEG) in water (e.g. from about 1% to about 10%, e.g. about 1, 2, 3, 4, 5, 6, 7, 8, 9 or 10% PEG in water); other alcohols such as methanol, isopropanol, etc., or other polar liquids such as acetonitrile, dimethylsulfoxide (DMSO), etc.

The concentration of GO in the medium that is irradiated is generally in the range of from about 0.1 mg/mL (or even less) to about 10 mg/mL (or greater), and is usually in the range of from about 1 mg/mL to about 5 mg/mL.

Types of light energy that may be used in the production of graphene from GO include but are not limited to various sources of UV, VIS and/or IR radiation such as lasers, radiation from tungsten-halogen lamps, sunlight, mercury lamps, hydrogen lamps, etc. Any source that provides a suitable wavelength of light may be used in the practice of the invention If lasers are employed, the wavelength that is used is generally in the range of from about 100 to about 800 nm, or from about 300 to about 1100 nm, and may be, for example, about 193 nm, or about 266 nm, or about 248 nm, or about 308 nm, or about 355 nm, or about 532 nm, or about 980 nm, or about 1064 nm. The power of the laser radiation is generally in the range of from about 1 Watt (W) to about 10 W, and is generally in the range of from about 2 W to about 9 W, or even in the range of from about 3 W to about 8 W, i.e. about 1, 2, 3, 4, 5, 6, 7, 8, 9 or 10 W; and the frequency (i.e. number of cycles per second, "hertz" or "Hz") is generally in the range of from about 10 to about 50 Hz, or from about 20 to about 40 Hz, and may be about 30 Hz. Those of skill in the art will recognize that factors such as wavelength, power and frequency are interdependent. In one embodiment, the production of graphene from GO is carried out using a laser at 532 nm, 7M and 30 Hz; in another embodiment, a YAG laser is employed at 355 nm, 5 W and 30 Hz.

When radiation from a tungsten-halogen lamp (or similar source) is used, the power employed is generally in the range of from about 100 to 1000 W, and may be from about 200 to about 900 W, or from about 300 to about 800 W, or from about 400 to about 700 W, or from about 500 to about 600 W, with a power of about 500 W being frequently used.

The length of exposure of GO to the light energy will vary depending on the type and strength of radiation that is used, the concentration of GO in the suspension, and the solution volume. Generally, these variables are adjusted so that the time of radiation is in the range of from about 1 to about 10 minutes, i.e. about 1, 2, 3, 4, 5, 6, 7, 8, 9, or 10 minutes. Further, several cycles of irradiation may be used, e.g. from about 1 to about 10 or more cycles (i.e. about 1, 2, 3, 4, 5, 6, 7, 8, 9, or 10 cycles) with each cycle including an exposure of the GO to the source of radiation of at least about one minute or more, as described above.

Prior to exposing the GO to light energy, the GO may be exfoliated in order to separate the layers. This is generally accomplished by dispersing GO in water using ultrasonic or stirring until a clear well-dispersed solution is obtained with a golden yellow color.

The starting temperature at which the conversion of GO to graphene is carried out is generally ambient (i.e. room) temperature, i.e. about 20 to 25° C. (68 to 77° F.), although this need not always be the case. In some embodiments, the temperature may be higher (e.g. up to about 37° C.) or lower (e.g. as low as about 1-2° C.) while still successfully producing graphene. It is also possible to start with frozen GO solution (below 0° C., e.g. −50° C. or −10° C., etc.) and convert the frozen solution to liquid by the photothermal effect of GO. Those of skill in the art will recognize that an increase in starting temperature may accelerate the reaction whereas a decrease in initial temperature may slow the reaction rate, either of which may be desirable for particular applications.

In some embodiments, irradiation is carried out in a manner that results in the complete conversion of GO to graphene. However, this is not always the case. In some embodiments, one or more of the amount, duration, intensity and wavelength(s) of irradiation is adjusted or tuned so as to cause only partial deoxygenation of the GO, but not complete conversion to graphene. The result may be the partial deoxygenation of the GO, or the substantially complete deoxygenation of GO, producing graphene. In other words, as those of skill in the art will recognize, the deoxygenation of GO to graphene need not be an "all or nothing" event. To be "substantially complete" usually at least about 75%, 80%, 85%, 90%, 95%, 99%, or even up to about 100% of the GO is converted to graphene.

In one embodiment, the graphene is produced using lasers, and what is produced is thus termed "laser converted graphene" or "LCG". In one embodiment, individual (single) LCG sheets are produced by laser reduction of exfoliated GO in water, and the reaction is carried out under ambient conditions (e.g. at room temperature, which is about 20-25° C.).

The progress of the reaction may be monitored by any suitable method, examples of which include but are not limited to UV-VIS spectral data, FTIR, Raman spectroscopy, etc.

Once the reaction has proceeded sufficiently, the source of radiation is withdrawn or removed and the graphene sheets are removed from the reaction mixture. For example, the solution may be centrifuged and the graphene separated after centrifuging, or the solution may be filtered to separate the graphene sheets, etc. The graphene may be rinsed (e.g. with water or another solvent, e.g. an alcohol), dried and stored for further use.

Using Solid GO

In another embodiment, the GO that is utilized to produce graphene is solid GO. In this embodiment, metal powder or nanoparticles are mixed with GO to form a mixture that is, e.g. pressed into a pellet (cake, block, layer, sheet, etc.) using high pressure. The mixed pellet is then used for the laser desorption process as described above, and metal-graphene nanocomposites are formed. In one embodiment, GO solid target is converted into graphene by the Laser Vaporization Controlled Condensation (LVCC) method as described in U.S. Pat. Nos. 5,580,655; 5,695,617; 6,136,156, 6,368,406 and 7,413,725, the complete contents of which are incorporated herein by reference.

The graphene sheets produced by both the "in solution" and "solid GO" methods may be used in any of a variety of applications and as components of a variety of apparatuses, e.g. they may be used in nanoelectronics, supercapacitors, batteries, photovoltaics, LEDs, and related devices.

II. Metals and Semiconductor Materials Supported on Graphene

The properties of graphene such as the high thermal, chemical, and mechanical stability as well as a high surface area, also represent desirable characteristics for its use as a 2-dimensional catalyst support for metallic and bimetallic nanoparticles. The invention also provides methods for producing graphene sheets which support one or more metal atoms, e.g. for use in catalyzing a variety of chemical reactions and transformation, particularly at high temperature. The main advantage of using the photochemical and photothermal reduction methods described herein to prepare metal nanoparticles supported on graphene is to avoid the use of toxic chemical reducing agents and thus provide a green approach for the synthesis and processing of metal-graphene nanocomposites. Also, for applications in catalysis, the absence of traces of reducing or capping agents from the surface of the supported nanocatalysts is advantageous. In addition, the present methods provide better control of the reduction processes without the need of high temperatures, and the possibility of the facile simultaneous reduction of two or more different metal ions on the graphene surface which could produce graphene nanocomposites with desirable catalytic, magnetic and optical properties.

The production of metal-graphene nanocomposites may be carried out using either GO dispersed in a liquid medium or solid GO. Generally, the overall procedure is the same as that which is described above for the production of graphene. However, in this embodiment, what is irradiated is a mixture of GO plus at least one metal of interest. Generally, when the GO is dispersed in a liquid solution, soluble metal salts are used. When solid GO is used, metal powder or nanoparticles are mixed with GO to form a mixture that is, e.g. pressed into a pellet using high pressure pellet production. The mixed pellet is then used for the laser desorption process as described above for the LVCC method. In the presence of metal ions, upon exposure to light energy as described herein, simultaneous reduction of the GO and metal ions takes place and metal-graphene nanocomposites are formed.

Examples of metals that may be used include but are not limited to Pd, Co, Au, Ag, Cu, Pt, Ni, Fe, Mn, Cr, V, Ti, Sc, etc and rare earth metals such as Ce, Pr, Nd, Sm, Gd, Hom Er, Yb, etc., and other metals such as Al, Ga, Sn, Pb, In, Mg, Ca, Sr, Na, K, Rb, Cs, etc. Also, semiconductors can be used such as Si, Ge, CdSe, CdS, CdTe, ZnO, ZnS, ZnSe, etc. Generally, the metals are provided as salts, i.e. with a negative counterion such as $Cl^-$, $NO_3^-$, sulfate, chlorate, borate, acetate, etc. In some embodiments, two or more metals are included, i.e. the resulting catalyst is bi-metallic (or tri-metallic, etc., depending on how many metals are present). Exemplary combinations of metals include but are not limited to: Pd plus Co; Au plus Ag, Pd plus Pt, Cu plus Pd, Pt plus Fe, etc.

The metals in the mixture that is irradiated are generally in the form of e.g. metal salts, and the concentration of the metal ions is generally in the range of from about 1% to about 20-30%, depending on, for example, the desired density of metal on the graphene sheet that is formed.

Metal catalysts supported on graphene sheets made according to the methods described herein may be used for any of a variety of purposes, including but not limited to catalysis, e.g. for use in Fischer-Tropsch Synthesis, hydrogen production reactions, CO oxidation, etc., as well as for sensors, hydrogen storage, energy conversion, and for other applications.

In another embodiment, semiconductor materials mixed with and irradiated with the GO and graphene sheets with associated semiconductor particles are formed. Examples of such substances include but are not limited to silicon, titanium and zinc oxides, CdSe, ZnS, CdS, etc. The conditions for carrying out such reactions are generally the same as those for the simultaneous reduction of GO and metal ions as described above. When Si is used, the concentration of Si in the mixture that is irradiated is generally from about 1% to about 20%, and the Si is generally in the form of Silicon powder or Si nanoparticles. Similar concentrations are used for the other semiconductor materials. Further, in some embodiments, semiconductor materials may be reduced together with GO and one or more metals of interest as described above.

III. Production of Heat

In one embodiment, the invention provides a method for the very high efficiency conversion of visible, infrared and ultraviolet radiation into thermal energy, i.e. heat. In this embodiment, graphite oxide and graphene as well as their metal and semiconductor nanocomposites, are exposed to light energy, and, as a result, heat is produced via a photothermal coupling reaction. The invention provides methods and apparatuses for generating heat by this method. The materials that are used in this embodiment of the invention include but are not limited to GO, graphene, and metal and semiconductor nanocomposites of GO and graphene. Exemplary metal and semiconductor nanocomposites of GO and graphene include but are not limited to those formed with gold, silver, palladium, copper, platinum, silicon, titanium dioxide, zinc oxide, etc. These materials may be referred to herein as "GO, graphene and nanocomposites thereof" or as "photothermally active materials", etc.

This embodiment of the invention has applications in a wide variety of scenarios, including but not limited to phototherapy in the medical field, for the production of heat in general, e.g. for domestic purposes, and for desalination of water. Each of these exemplary uses is discussed below.

Phototherapy

In some embodiments related to phototherapy, the method involves: 1) identification of a patient or subject in need of phototherapy (e.g. a subject with unwanted cells or tissues such as hyperproliferating cells of tissues (e.g. cancerous tumors, etc.); 2) identification of one or more locations within or on the body of the patient where the application of heat would be beneficial (e.g. in the environs of a tumor); 3) placement of GO, graphene and/or one or more nanocomposites thereof at the identified location(s) where it is desired to produce heat (e.g. at, near, on, within or adjacent to cancerous tumor cells or other tissue that is unwanted and for which destruction of the tissue or cells is desirable); and 4) irradiation of the GO, graphene and/or one or more nanocomposites with a suitable wavelength of electromagnetic radiation. The interaction of the GO, graphene and/or one or more nanocomposites with the incident radiation causes the generation of intense heat at the targeted area, and the targeted, unwanted cells or tissues at or in the vicinity of the targeted area are harmed or destroyed (killed). In some embodiments, irradiation is carried out only once whereas in other embodiments, irradiation is carried out repeatedly at spaced-apart intervals, i.e. the targeted area is subjected to repeated cycles of radiation. The amount of GO, graphene and/or one or more nanocomposites at the irradiated (targeted) site(s) may be varied or adjusted so as to influence the amount of heat that is generated, thus lending a high level of flexibility to the method. Thus, the amount of heat that is generated at any given time or site can be modulated in a flexible manner, e.g. increased or reduced, as required or desired, by varying one or both of 1) the amount of GO, graphene and/or one or more nanocomposites at the irradiated site; and 2) the frequency, duration, intensity, and particular wavelengths of radiation that are used.

In some embodiments, a laser is used as the radiation source. When a laser is used, it is possible to narrowly focus the radiation, pinpoint the targeted area, and avoid irradiating surrounding tissue. Those of skill in the art will recognize that the use of lasers for phototherapy or similar purposes in known. However, by using the methods described herein, the phototherapy can be carried out much more rapidly and efficiently, and even areas that are otherwise difficult to access may be targeted. Exemplary uses for this aspect of the technology include but are not limited to applications in phototherapy (e.g. for the treatment of cancer; treatment of macular degeneration; etc.); as well as for the destruction or removal of unwanted fatty deposits (e.g. in arteries) or fatty tissue (e.g. for cosmetic surgery); unwanted pigments, hair follicles, diseased or dead tissue, hyperproliferating cells or tissue, etc.

Production of Heat for Other Purposes

Figure 22:
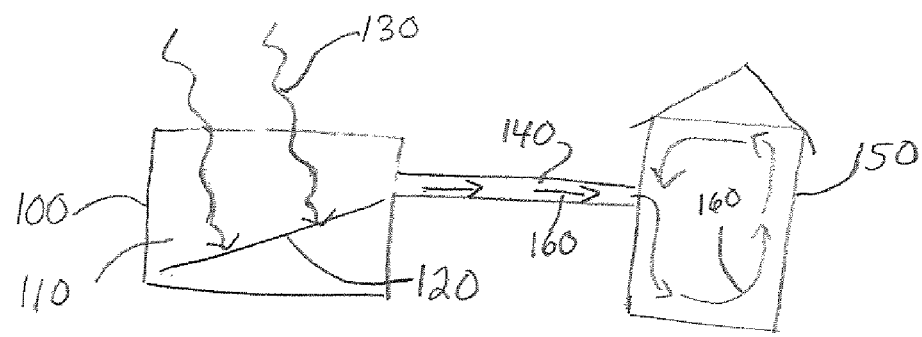
FIG. 22. Schematic depiction of apparatus and system for production of heat by the methods of the invention.

In some embodiments, the heat generating properties of the invention are used for applications in which the heat that is generated from the reaction is captured or conserved and then used for heating on a large scale, e.g. for domestic or commercial heating. In this embodiment, one or more of the materials described herein (GO, partially reduced GO, graphene and/or one or more nanocomposites thereof) are incorporated into an apparatus in a manner that permits or facilitates exposure of the material to a source of light energy. In one embodiment, the source of light energy is sunlight, although this is not always the case. The material that is exposed to light energy is generally in the form of a suspension of the material in a medium that absorbs or captures the heat (e.g. a liquid medium such as water, or in some embodiments, a gaseous medium such as air). In some embodiments, once heated, the medium is moved or circulated to an environment that is to be heated via transfer of the heat from the medium to the environment. Alternatively, the graphene material may be in the form of a sheet which is submerged in or coated with e.g. a liquid medium. Significantly, as demonstrated in the Examples section below, the graphene materials can be used repeatedly and/or regenerated for repeated uses without degradation or loss of efficiency. This embodiment of the invention may be implemented in such apparatuses as e.g. hot water or steam heating systems (e.g. boilers), and the like. FIG. 22 shows a schematic depiction of an exemplary embodiment of this type. In this embodiment, container 100 contains heatable medium 110 (e.g. water, other liquid medium, air, etc.) and photothermally active material 120 (GO, partially reduced GO, graphene and/or one or more nanocomposites thereof). Incident light 130 (e.g. sunlight) impinges on 120, and heat is generated by photothermally active material 120. Surrounding heatable medium 110 is heated and transported via conduit 140 to a location where the heat is released from heated medium 160, e.g. to destination such as dwelling 150, where heated medium 160 circulates and releases heat.

In one exemplary embodiment, the heat (and/or optionally light) that is produced is used directly, e.g. to heat homes or dwellings, e.g. for humans or other life forms that do not thrive in or are generally adverse to the cold. In some embodiments, such dwellings may be conventional (e.g. houses, dormitories, buildings for livestock or other animals, etc.) or for heating greenhouses or orchards (e.g. to prevent the loss of crops such as citrus crops during a freeze), for desalination (discussed below), etc. Heating units employing the technology of the invention may be "built-in" to a structure, or may be portable (mobile). Other less conventional applications may occur to those of skill in the art, e.g. heating aircraft, space ships, space stations, and underwater vessels (e.g. submarines) where the flexibility and portability of the methods and apparatuses would be a distinct advantage. For applications where sunlight is not available, the photothermal cells or arrays may be activated by exposure to an alternative light source, e.g. laser, tungsten-halogen lamp, etc.

Figure 23:
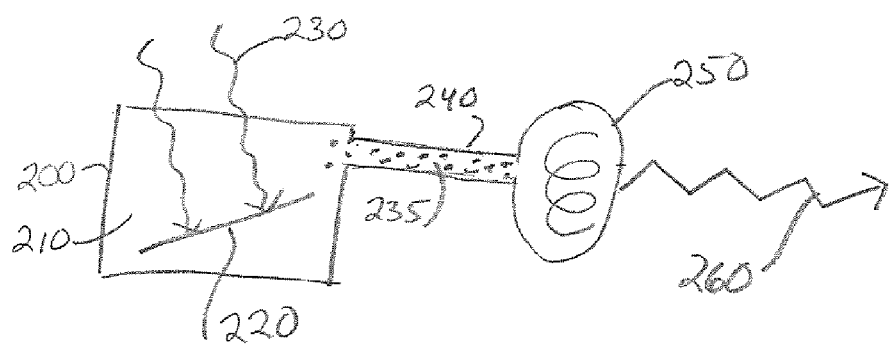
FIG. 23. Schematic depiction of apparatus and system for generation of electricity by the methods of the invention.

In other embodiments, the heat that is generated as described herein may be used, e.g. to heat substances (e.g. liquids) such as water for any use (e.g. in homes, recreational facilities, business, etc.) or to create steam for heating, or for the generation of electricity (e.g. via a steam turbine connected to an electrical power generator), etc. This embodiment is schematically depicted in FIG. 23, which shows container 200 which contains medium 210 (e.g. water) and photothermally active material 220 (GO, partially reduced GO, graphene and/or one or more nanocomposites thereof). Incident light 230 (e.g. sunlight) impinges on photothermally active material 220, and sufficient heat is generated by photothermally active material 220 to form steam 235 from medium 210. Steam 235 is transported via conduit 240, e.g. to steam turbine 250, where electricity 260 is generated.

Alternatively, the methods and apparatuses have application in manufacturing, where the heat may be used to drive chemical reactions for the synthesis of various products (e.g. by heating the reaction components or the medium in which the reaction is carried out, by creating steam, etc.

Advantageously, the materials used to generate heat in this manner can be regenerated after several cycles of exposure to light energy, and then reused with high efficiency. Regeneration is accomplished e.g. by washing, filtration or centrifuging if necessary and/or by re-oxidizing the graphene or graphene nanocomposite, etc.

Additional Applications for the Generation of Heat Using the Methods of the Invention This method of heat generation can be applied for other purposes as well, e.g. those where the targeted generation of heat at a distance is desired or advantageous. For example, photothermal reactive material placed in an explosive device can be irradiated from a distance (e.g. with a laser), causing detonation of the device from a distance. Examples of this application include but are not limited to uses by the military during warfare, in excavations, or during construction and mining where the removal of earth or rock, etc. is required, etc.

In addition, the materials and methods of the invention may be used in a variety of scenarios where it is desirable to produce heat above and beyond that which is supplied by exposure to sunlight. In all such embodiments, the photothermally active materials as described herein may be used in any of a variety of forms, e.g. as particles, sheets, discs, etc, or as coatings or paints, or other wise attached to or incorporated into an item. For example, the materials described herein may be used to replace e.g. carbon black in various applications such as those described in U.S. Pat. Nos. 6,508,247; 6,827,772; 7,255,134; and 7,820,865, the complete contents of each of which are herein incorporated by reference. For example, graphene polymer composites may be used to coat or otherwise be incorporated into materials used for building or heating swimming pools, aquaria, algae ponds, etc. (e.g. pipes, floating, removable, or stationary panels; liners; cement; concrete; tiles; etc.). In cold climates, the materials may be advantageously incorporated into building materials (e.g. roofing, siding, materials for banking a building during winter, etc.). Further, the materials may have applications for use in fabric or clothing (e.g. cold weather footwear, jackets, sweaters, hats, etc. or in items intended for emergency e.g. blankets); in materials for use in accelerating the removal or melting of snow and ice, e.g. tarps or sheets of materials that can be placed on e.g. a sidewalk, or placed on or incorporated into a vehicle, especially a vehicle that is primarily used during cold conditions; or used to protect trees or crops during a freeze; or for use in camping material, e.g. tents, sleeping bags, etc.; or in cooking materials (e.g. pots) or in stoves or ovens, particularly in areas where sources of fuel are scarce; or even for novelty items to cause an increase in heat that is surprisingly out of proportion to incident sunlight. The materials of the invention may be used in any circumstance where sunlight is available and where it is desired to efficiently provide photothermal heating.

However, for these applications it is not absolutely to have access to sunlight, as suitable wavelengths of radiant energy may also be supplied by other sources (lamps, flashlights, laser sources, etc. as described herein). Thus, by coupling the materials and methods with a suitable source of radiant energy, efficient photothermally induced heating can be provided in any environment even in the absence of sunlight. For example, in cold climates, the interiors of buildings (walls, floors, ceilings, etc.) can be efficiently heated upon exposure to suitable wavelengths of radiant energy, if coated or lined with the materials described herein. Likewise, covers for foods (e.g. in a restaurant or cafeteria) may be made from or coated with photothermally active materials and heated when exposed to one or more suitable wavelengths of radiation.

In all embodiments involving heating, the photothermally active materials as described herein may be used in any of a variety of forms, e.g. as particles, sheets, discs, etc, or as coatings or paints, or other wise attached to or incorporated into an item, so long as they are positioned or located so as to provide heat in a suitable manner. For example, particles of the materials may be mixed with water (e.g. in a swimming pool), and optionally, agitated to distribute the particles; or materials which make up the pool may be coated with photothermally active materials, etc. The latter approach may have advantages in that particulate material may be more difficult to remove if required, e.g. to clean the system.

Other applications of this technology will occur to those of skill in the art, and all such applications are encompassed by the present invention.

Desalination

In one embodiment of the invention, the heat-generating capability of the technology is used in the process of desalination, i.e. for the removal of salts and other minerals from water that contains unacceptably high levels of these substances. In an exemplary embodiment, the technology is used for the desalination of sea water in order to produce desalinated water that is suitable for consumption (e.g. by humans, livestock, etc.) and/or for irrigation. The technology is especially well adapted to geographical locations which have ample sunshine but where there is a scarcity of sources of fresh water. In all embodiments involving desalination, the photothermally active materials as described herein may be used in any of a variety of forms, e.g. as particles, sheets, discs, etc, or as coatings or paints, or other wise attached to or incorporated into an item, so long as they are positioned or located so as to heat the contaminated water. For example, particles of the materials may be mixed with sea water, and optionally, agitated to distribute the particles; or a container in which sea water is present may be coated with the photothermally active materials, etc. The latter approach may have advantages in that particulate material may be more difficult to remove if required, e.g. to clean the system.

In this embodiment, the heat produced by the methods described herein is used to heat water which contains unwanted materials (e.g. salts, minerals, chemicals, etc., for example, sea water, brackish water, water discharged from manufacturing facilities, water contaminated with feces or microbes, etc.) sufficiently to cause evaporation of water vapor, leaving behind the salts, minerals and/or contaminants. The water vapor is captured and condensed to produce "fresh" water. In some embodiments, the methods of the invention are used to heat the water to at least from about 70 to about 80° C., and then a second energy source is used to supply further heating. This embodiment still provides significant energy savings by decreasing the amount of heat required from the second energy source.

Alternatively, or in addition, in some embodiments, water vapor produced by this method is used as a source of humidity e.g. to produce humidified air, instead of or in addition to producing water. The method also provides apparatuses capable of carrying out these reactions. Such an apparatus comprises at least: means (e.g. a container) for containing at least one photothermally active material of the invention (GO, graphene and/or metal or semiconductor nanocomposites thereof) and water which contains salt and/or unwanted minerals or chemicals; means for irradiating the combined material and water (if artificial sources of light energy are used) or means for allowing exposure of the water to natural sunlight (e.g. through transparent glass or polymer material); means for capturing water vapor which evaporates from the salt and/or mineral or chemical laden water (e.g. a water vapor collector); means for condensing the water vapor (e.g. a condenser); and means for capturing and containing the pure water that is produced by condensation of the water vapor (e.g. a collection vessel). Alternatively, the salt and/or mineral laden water may not come into direct contact with the photothermally active material, but may be heated indirectly by transfer of heat from another liquid that is heated by the photothermal energy conversion.

Figure 24:
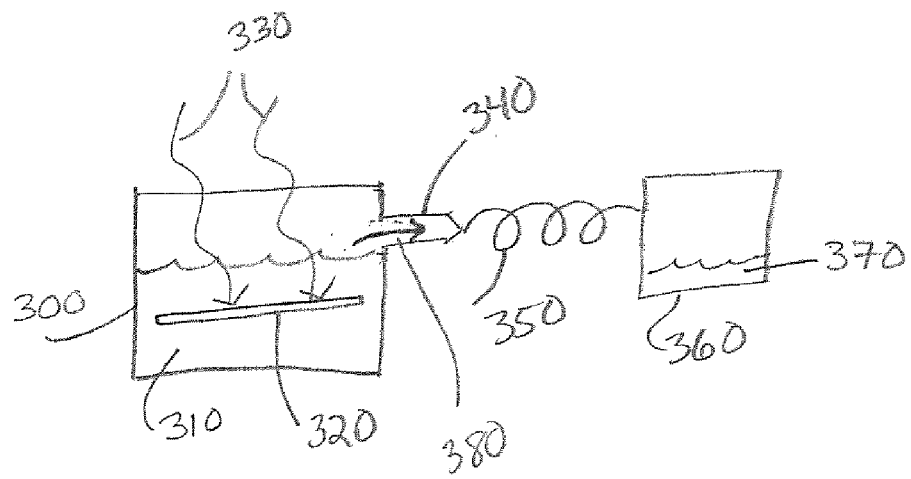
FIG. 24. Schematic depiction of apparatus and system for desalination by the methods of the invention.

An exemplary desalination apparatus is depicted in FIG. 24. In this Figure, container 300 contains e.g. seawater 310 and photothermally active material 320. Incident light energy (e.g. sunlight) 330 falls on photothermally active material 320, which produces heat, thereby heating seawater 310. Water vapor (represented by arrow 380) is created and transported by optional conduit 340 to condenser 350, which condenses the water vapor. Receptacle 360 receives (catches, contains, etc.) condensed fresh water 370. Those of skill in the art will recognize that some elements of the apparatus are optional or may be combined, e.g. condenser 350 may be located within or part of conduit 340, or condenser 350 may be located in or part of receptacle 360, etc. Various other conduits, valves, pipes etc. may be employed in the apparatus, and any or all of these components may also be coated with or have incorporated therein the photothermally active material described herein, e.g. a GO or graphene-polymer composition may be used to coat or manufacture pipes.

In one embodiment, the materials of the invention are employed in solar humidification-dehumidification (HDH) methods for thermal water desalination. HDH is based on evaporation of sea water or brackish water and consecutive condensation of the generated humid air, mostly at ambient pressure, thereby mimicking the natural water cycle, but over a much shorter time frame. The simplest configuration is implemented as a solar still, evaporating the sea water inside a glass or other suitable polymer covered container, and condensing the water vapor on the lower side of the cover, from which it is captured. More sophisticated designs separate the solar heat gain section from the evaporation-condensation chamber. An exemplary optimized design may comprise separated evaporation and condensation sections. A significant part of the heat consumed for evaporation can be regained during condensation. An example of an optimized thermal desalination cycle is the multiple-effect humidification (MEH) method. MEH uses multiple evaporation-condensation cycles at separate temperature levels to minimize the total energy consumption of solar humidification processes.

Other technologies into which the materials of the present invention can be incorporated include but are not limited to "Seawater Greenhouse" technology, which involves using seawater to humidify and cool the air inside a greenhouse, and also to produce fresh water by distillation (evaporation by solar heating and subsequent condensation).

IV. Production of Electricity and/or Light

Figure 20:
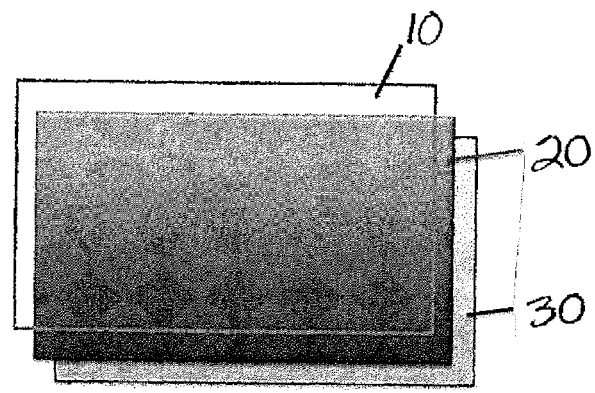
FIG. 20. Fabrication of photovoltaic (PV) and optionally light-emitting diode (LED) devices using dual purpose graphene substrates.

The graphene and graphene nanocomposites produced by the methods of the invention also have applications for the production of electricity and light, and the invention also provides methods and apparatuses for the production of electricity and/or light. Applications of this facet of the invention include the production of photovoltaic devices, circuits, photodiodes, photodetectors, photoconductors, charge-coupled devices, photomultiplier tubes and the like, which are frequently used in consumer electronics devices. Such apparatuses may be designed in a fashion that is or is similar to that of photovoltaic cells or arrays, i.e. as cells or arrays. A schematic of an exemplary photovoltaic cell of the invention is depicted in FIG. 20. This figure shows transparent conducting layer 10, photoabsorber 20 and back electrode 30, one or more of which incorporates one or more graphene or graphene-metal or graphene-semiconductor composites produced as described herein. Transparent conducting layer 10 is generally a glass or polymer substrate into or onto which the materials of the invention (e.g. a graphene monolayer or graphene-metal monolayer made by the methods described herein) may be loaded or positioned. Graphene monolayer fabricated as described herein are both transparent and conductive, and may replace indium tin oxide (ITO)-coatings which can be extremely problematic, suffering from price volatility, sustained high cost, and limited worldwide availability. Photoabsorber 20 further comprises, for example, a graphene-semiconductor nanocomposite made as described herein. Back electrode 30 generally comprises graphene (typically a graphene monolayer produced as described herein) and/or metallic ink.

In some embodiments, when sunlight is to be used as the incident energy source, such cells or arrays of such cells are arranged in suitable locations such as on rooftops or areas exposed to sunlight without interference (e.g. open lands). However, many other configurations may also be employed, including portable versions of the cells or arrays.

Figure 25:
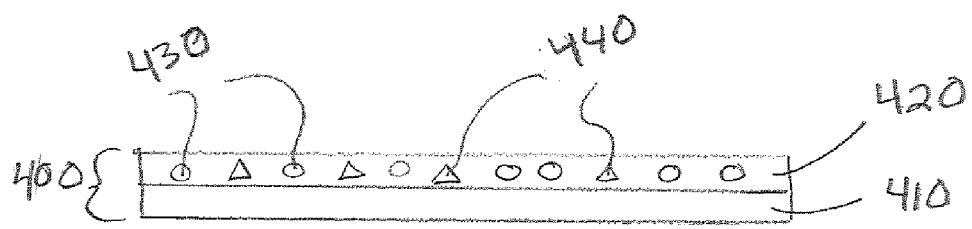
FIG. 25. Schematic depiction of light-emitting-diode (LED) of the invention.

In addition, those of skill in the art will recognize that the graphene sheets described herein may also be employed in the fabrication of LEDs. When the objective is to produce light, the invention provides LEDs comprising a substrate (e.g. a chip), and a semiconductor nanocomposite of graphene associated with the substrate. The LEDs are made by the methods and processes described herein fore the generation of graphene from GO. The semiconductor nanocomposite of graphene is doped with impurities to create one or more p-n junctions (positive-negative junctions) on the substrate. As in other types of diodes, current flows easily from the p-side (anode) the n-side (cathode) but not in the reverse direction. Charge-carriers, i.e. electrons and holes, flow into the junction and when an electron encounters a hole, it falls into a lower energy level, releasing energy in the form of a photon. An exemplary LED 300 is depicted in FIG. 25, which shows substrate 410 with associated graphene layer 420 (e.g. a semiconductor nanocomposite of graphene) having associated semiconductor nanoparticles 430, and doped with impurities 3440.

In some embodiments, a single device may be fabricated which advantageously produces both heat and light.

While the invention has been described in terms of various embodiments, other variations of this technology will occur to those of skill in the art, and all such variations are encompassed by the invention. The following Examples serve to further illustrate the invention but should not be construed as limiting the subject matter in any way.

EXAMPLES

Example 1. Photothermal Deoxygenation of Graphite Oxide with Laser Excitation in Solution and Graphene-Aided Increase in Water Temperature This example describes the development of a facile laser reduction method for the synthesis of laser converted graphene (LCG). The method provides a solution processable synthesis of individual graphene sheets in water under ambient conditions without the use of any chemical reducing agent. We also report on the high performance of GO and graphene for the efficient conversion of the laser radiation into usable heat, particularly for heating water for a variety of potential thermal, thermochemical, and thermomechanical applications.

The XRD pattern of the exfoliated GO is characterized by a peak at 2θ 10.9 with a larger d-spacing of 8.14 Å (compared with the typical value of 3.34 Å in graphite) resulting from the insertion of hydroxyl and epoxy groups between the carbon sheets and the carboxyl groups along the terminal and lateral sides of the sheets as a result of the oxidation process of graphite.[13-15,18] Following a 532 nm laser irradiation, the yellow golden color of a GO solution changes gradually to brown and finally to black (not shown), with the concomitant decrease and finally the complete disappearance of the 2θ=10.9 peak (FIG. 1A), thus confirming the deoxygenation of the GO sheets and the restoration of the $sp^2$ carbon sites in the LCG.[14,15] A similar result was obtained following irradiation using the third harmonic of the YAG laser (355 nm, 5 W, 30 Hz), as shown in FIG. 1B. The XRD patterns displayed in FIG. 1B indicate clearly that the graphite peak at 2θ=27.9 is not present in the GO sample before and after the disappearance of the 2θ=10.9 GO peak, indicating the absence of graphite or multilayer graphene. The irradiation time required for the deoxygenation of GO using the 532 or the 355 nm lasers varies from a few to several minutes depending on the laser power, the concentration of GO, and the volume of the solution. Experiments using the fundamental of the YAG laser (1064 nm, 30 Hz, 5 W) resulted in a rapid partial deoxygenation of the GO but with no change in the color of the solution, suggesting no conversion to graphene, as evidenced by the non-disappearance of the XRD 2θ=10.9 peak of GO, as shown in FIG. 1C. At higher laser power (7 W, 30 Hz), the solution was bleached after 5 to 6 min with the evolution of gases, most likely $CO_2$ and $H_2O$ vapors, and the formation of a graphitic powder indicating the decomposition of GO. With the 355 nm irradiation, bleaching of the black solution was observed at longer irradiation times (after 6 to 7 min using an average power of 5 W, 30 Hz). However, with the 532 nm irradiation, no bleaching was observed, even after 10 min of irradiation using an average power of 7 W at a repetition rate of 30 Hz.

To understand the nature of the species absorbing the laser energy and to elucidate the mechanism of the laser deoxygenation of GO, we measured the UV-vis spectrum of GO in water and compared it with the spectra of the LCG produced following the 532 and 355 nm laser irradiation of GO, as shown in FIG. 2A. The UV absorption spectrum of GO (FIG. 2A) shows significant absorption below 400 nm with the characteristic shoulder at 305 nm attributed to n→π* transitions of C=O bonds. Clearly, this would facilitate the absorption of the 355 nm irradiation. However, for the 532 nm irradiation, two-photon absorption would probably contribute significantly to the absorption of laser energy by GO. The nonlinear optical (NLO) and optical limiting (OL) properties of GO and graphene have been recently investigated using nanosecond and picosecond laser excitations.[4,5] These studies show that excited-state nonlinearities play an important role in enhancing the NL absorption of GO at 532 nm in the nanosecond regime.[4] GO does not show any NLO responses at 1064 nm,[5] consistent with our observation of no reduction of GO taking place following the 1064 nm irradiation in water.

It is important to note that the characteristic shoulder of GO at 305 nm disappears after the 532 nm or the 355 nm irradiation of GO (FIG. 2A), and the absorption peak of GO at 230 nm red shifts to ~270 nm because of the π→π* transitions of extended aromatic C—C bonds, thus suggesting that the electronic conjugation within the graphene sheets is restored in the LCG. The gradual red shift of the 230 nm peak of GO and the increase in absorption in the whole spectral region (230 nm) can be observed as a function of the laser irradiation time, as shown in FIG. 2B. The red shift and the increase in absorption do not show much change after 10 min of laser irradiation, indicating complete deoxygenation of GO and formation of LCG within 10 min under the conditions described in the Experimental Section. A similar result was obtained using the 355 nm laser irradiation (not shown). The observed trend suggests that the laser irradiation method can provide a way to tune the degree of deoxygenation of GO because the extent of the red shift is related to the degree of aromaticity in the LCG. A similar trend was observed for the hydrazine hydrate reduction of GO, where gradual red shift of the 231 nm peak to 270 nm and an increase in the absorption in this region were observed as a function of reaction time. However, in the CCG using hydrazine hydrate reduction, the reaction was completed after 1 h at 95° C., as compared with 10 min at room temperature for the current LCG method.

In addition to the XRD and UV-vis data, the successful conversion of GO into LCG using the 532 and 355 nm irradiation was further verified by FT-IR, X-ray photoelectron spectroscopy (XPS), and Raman spectroscopy, as shown in FIG. 3. FIG. 3A compares the FT-IR spectra of GO and the LCG. The GO spectrum shows strong bands corresponding to the C=O stretching vibrations of the COOH groups at 1740 $cm^{-1}$, the O—H deformations of the C—OH groups at 1350-1390 $cm^{-1}$, the C—O stretching vibrations at 1060-1100 $cm^{-1}$, and the epoxide groups (1230 $cm^{-1}$). These bands were completely absent from the spectrum of the LCG, thus confirming the conversion of GO to graphene following the 532 nm laser irradiation of GO in water.

The XPS C1s spectrum of GO shows peaks corresponding to oxygen-containing groups between 285.5 and 289 eV in addition to the $sp^2$-bonded carbon C=C at 284.5 eV (FIG. 3B). Typically, peaks at 285.6, 286.7, 287.7, and 289 eV are assigned to the C1s of the C—OH, C—O, C=O, and HO—C=O groups, respectively. The XPS data of the LCG clearly indicate that most of the oxygen-containing groups in GO are removed after the 532 nm laser irradiation of GO in water (FIG. 3B).

The Raman spectra of the prepared GO and LCG are shown in FIG. 3C. The spectrum of the exfoliated GO shows a broadened and blue-shifted G-band (1594 $cm^{-1}$) and the D-band with small intensity at 1354 cm–1 (as compared with graphite). The spectrum of the LCG shows a strong G-band around 1572 $cm^{-1}$, almost at the same frequency as that of graphite with a small shoulder, identified as the D0-band around 1612 $cm^{-1}$, and a weak D-band around 1345 $cm^{-1}$. The D-band and the D0-shoulder have been attributed to structural disorder at defect sites and finite size effects, respectively.[6,7] The intensity ratio of the D-band to the G-band is used as a measure of the quality of the graphitic structures because for highly ordered pyrolitic graphite, this ratio approaches zero[7] As shown in FIG. 3C, the Raman spectrum of the LCG sheets exhibits a weak disorder-induced D band with the D-to-G intensity ratio of ~0.29, as compared with 0.67, thus indicating a significant reduction of the degree of disorder and defect sites following the laser deoxygenation of GO.[7]

TEM images of the LCG sheets (not shown) show wrinkled and partially folded sheets with a lateral dimension of up to a few micrometers in length. AFM images with cross-section analysis show that most of the flakes consist of a single graphene sheet. The vertical heights of the sheet at different lateral locations were determined to be 0.99, 1.03, and 1.02 nm. This is consistent with the reported AFM results on graphene, where the single layer graphene is ~1 nm.

The temperature changes caused by the photothermal conversion of GO in water during the laser irradiation are shown in FIGS. 4A and B. The comparison with pure water experiments under identical laser irradiation conditions clearly demonstrates the high performance of GO for the photothermal conversion of energy. The blank sample of water did not undergo any significant temperature change upon irradiation with 532 or 355 nm for 10 min (FIG. 4A), but the temperature of GO solutions rose above 60° C. under the same conditions (532 nm, 5 W, 30 Hz, FIG. 4B). This remarkable optothermal conversion for the GO solution corresponds to a 40° C. increase in temperature. Using the molar heat capacity of liquid water (75.3 J/mol ° C.), the amount of heat transferred to the 3 mL of water causing a 40° C. increase in temperature can be estimated to be 502 J, which amounts to >16% of the used laser energy (5 W, 10 min irradiation). This high efficiency of heat transfer to water is attributed to the extremely high value of the thermal conductivity of graphene (up to 5300 W/mK at room temperature), which suggests that graphene can outperform carbon nanotubes (CNTs) in heat conduction.

The strong absorption of the IR radiation by water and the very weak absorption of the IR photons by GO prevent the conversion of GO to graphene, consistent with the flash experiments of GO films, where much higher flash energies were needed in the presence of water vapor.[1] However, at higher flash energies, decomposition of GO to graphitic carbon takes place (~200° C.) before the conversion to graphene.[2] In the current experiments with 532 nm (7 W, 30 Hz), GO is converted to graphene, and the temperature of water rises to over 75° C. in a few minutes without decomposition of the LCG (not shown). The shorter excitation wavelength of 355 nm is strongly absorbed and good for heating the GO surface, but the GO solution bleaches out at higher laser power and longer irradiation times (>5 W, 30 Hz, and >6 min). This indicates that the 532 nm irradiation is more efficient for obtaining rapid photothermal energy conversion by GO in water. It is important to note that in the case of the IR irradiation, the increase in the temperature of the GO solution is mainly due to the absorption of the IR photons by water. However, heating the water with the 1064 nm irradiation even to 75° C. is not sufficient to deoxygenate GO and produce graphene, as shown by the no change observed in the color of GO after the 1064 nm irradiation. Also, the UV-vis spectra of GO before and after the 1064 nm irradiation are identical (not shown). To confirm that deoxygenation of GO does not take place simply by heating it in water, we heated a solution of GO in water to the boiling point for more than 1 h, and no changes were observed in the GO, as indicated by the identical UV-vis spectra obtained before and after heating.

The advantage of the 532 nm (or the 355 nm) irradiation is that it efficiently converts GO to the more thermally and chemically stable graphene with integrated electronic conjugation. Because of the stability of graphene and its stronger NLO and OL properties as compared with GO,[5] repeated irradiation cycles can be performed with no loss of photothermal conversion efficiency (not shown). We were able to repeat the heating (laser on) and cooling (laser off) cycles reproducibly over seven cycles with almost the same temperature profiles (not shown). The temperature of the solution returns to room temperature after the laser is turned off at almost the same rate as heating occurs during laser irradiation. Furthermore, the photothermal energy conversion of the LCG (second irradiation cycle of GO) appears to be similar to that of CCG prepared by the hydrazine hydrate reduction of GO. These results demonstrate the very high stability of the LCG as a potential photothermal convertor for a variety of applications that require fast and efficient temperature rise. In fact, the first application of graphene composites in photothermal therapy has been reported very recently.[11] However; the laser reduction of GO in water, the accompanied significant temperature rise of water, and the repeated cycles of laser heating of the LCG have not been demonstrated prior to this work. It is reasonable to speculate that the demonstration of efficient photothermal energy conversion by GO and graphene would trigger several other applications in addition to photothermal therapy.

The observed temperature rise reflects the steady-state net heat transfer from the LCG to water following the deoxygenation of GO by photothermal energy conversion. Without being bound by theory, the suggested mechanism involves the absorption of the photon energy at 532 or 355 nm by GO resulting in the formation of a heated electron gas that subsequently cools rapidly (picosecond time scale) by exchanging energy with the GO lattice.[8,9] It has been shown that nanosecond pulse lasers are suitable for thermal confinement of absorbed energy.[8,9] In fact, the computed temperatures from pulse laser heating can be on the order of several thousand degrees.[9] However, for sufficiently long exposure times, the laser energy will be dissipated to the surroundings, and a steady state will be reached.[9] For example, in the flash exposure experiments of solid GO, a temperature of 400-500° C. was achieved within a few milliseconds.[2] Using the current nanosecond laser pulses, the temperature rise of the GO is expected to be much higher than 500° C., achieved by the flash light, which is sufficient to remove the oxygen containing functional groups from GO completely, thus resulting in the formation of LCG.

In summary, we have developed a facile chemical free laser reduction method using visible light irradiation in solution for the synthesis of LCG. Efficient photothermal energy conversion of GO and the thermally and chemically stable LCG has been observed, and the major parameters that control the energy conversion efficiency have been investigated. Despite the simple experimental approach, we made an important finding in that efficient heating of water can take place because of the high photothermal conversion efficiency of GO and LCG. This remarkable finding may open up the possibility of solar energy conversion to heat via graphene for the generation of steam and electricity as well as for thermochemical and thermomechanical applications.

Experimental Section

In the experiments, GO was prepared by the oxidation of high purity graphite powder (99.9999%, 200 mesh, Alfa Aesar) according to the method of Hummers and Offeman.[10] After repeated washing of the resulting yellowish-brown cake with hot water, the powder was dried at room temperature under vacuum overnight. Dried GO (2 mg) was sonicated in 10 mL of deionized water until a homogeneous yellow dispersion was obtained. GO solution (3 mL) was irradiated with a pulsed Nd/YAG laser (unfocused, second harmonic $\lambda=532$ nm, $h\nu=2.32$ eV, pulse width $\tau=7$ ns, repetition rate=30 Hz, fluence ~0.1 J/cm$^2$, Spectra Physics LAB-170-30) under continuous stirring. The temperature of the solution was monitored during the laser irradiation using a thermocouple immersed in the solution. The LCG sheets were separated and dried overnight under vacuum before the XRD, Raman, IR, and XPS measurements.

Characterization.

TEM images were obtained using a Joel JEM-1230 electron microscope operated at 120 kV equipped with a Gatan UltraScan 4000SP 4K 4K CCD camera. The small-angle X-ray diffraction (SA-XRD) patterns were measured at room temperature with an X'Pert Philips Materials Research diffractometer using Cu KR1 radiation. The XPS analysis was performed on a Thermo Fisher Scientific ESCALAB 250 using a monochromatic Al KR. Absorption spectra were recorded using a Hewlett-Packard HP-8453 diode array spectrophotometer. For the FT-IR spectra, a KBr (IR grade) disk containing either GO or LCG was prepared and scanned from 4000 to 500 cm$^{-1}$ using the Nicolet 6700 FT-IR system under transmission mode. The Raman spectra were measured using an excitation wavelength of 457.9 nm provided by a Spectra-Physics model 2025 argon ion laser. The laser beam was focused to a 0.10 mm diameter spot on the sample with a laser power of 1 mW. The samples were pressed into a depression at the end of a 3 mm diameter stainless steel rod held at a 30° angle in the path of the laser beam. The detector was a Princeton Instruments 1340 400 liquid nitrogen CCD detector attached to a Spexmodel 1870 0.5 m single spectrograph with interchangeable 1200 and 600 lines/mm holographic gratings (Jobin-Yvon). The Raman scattered light was collected by a Canon 50 mmf/0.95 camera lens. Although the holographic gratings provided high discrimination, Schott and Corning glass cutoff filters were used to provide additional filtering of reflected laser light, when necessary.

REFERENCES FOR BACKGROUND AND EXAMPLE 1

(1) Cote, L. J.; Cruz-Silva, R.; Haung, J. Flash Reduction and Patterning of Graphite Oxide and Its Polymer Composite. J. Am. Chem. Soc. 2009, 131, 11027-11032.
(2) Gilje, S.; Dubin, S.; Badakhshan, A.; Farrar, J.; Danczyk, S. A.; Kaner, R. B. Photothermal Deoxygenation of Graphene Oxide for Patterning and Distributed Ignition Applicatios. Adv. Mater. 2010, 22, 419-423.
(3) Zhang, Y.; Guo, L.; Wei, S.; He, Y.; Xia, H.; Chen, Q.; Sun, H.-B.; Xiao, F.-S. Direct Imprinting of Microcircuits on Graphene Oxides Film by Femtosecond Laser Reduction. Nano Today 2010, 5, 15-20.
(4) Liu, Z.; Wang, Y.; Zhang, X.; Xu, Y.; Chen, Y.; Tian, J. Nonlinear Optical Properties of Graphene Oxide in Nanosecond and Picosecond Regimes. Appl. Phys. Left. 2009, 94, 021902.
(5) Feng, M.; Zhan, H.; Chen, Y. Nonlinear Optical and Optical Limiting Properties of Graphene Families. Appl. Phys. Lett. 2010, 96, 033107.
(6) Ferrari, A. C. Raman Spectroscopy of Graphene and Graphite: Disorder, Electron-Phonon Coupling, Doping and Nonadiabatic Effects. Solid State Commun. 2007, 143, 47-57.
(7) Graf, D.; Molitor, F.; Ensslin, K.; Stampfer, C.; Jungen, A.; Hierold, C.; Wirtz, L. Spatially Resolved Raman Spectroscopy of Single- and Few-Layer Graphene. Nano Lett. 2007, 7, 238-242.
(8) Link, S.; El-Sayed, M. A. Optical Properties and Ultrafast Dynamics of Metallic Nanocrystals. Annu. Rev. Phys. Chem. 2003, 54, 331-366.
(9) Avedisian, C. T.; Cavicchi, R. E.; McEuen, P. L.; Zhou, X. Nanoparticles for Cancer Treatment. Role of Heat Transfer. Ann. N.Y. Acad. Sci. 2009, 1161, 62-73.
(10) Hummers, W. S., Jr.; Offeman, R. E. Preparation of Graphitic Oxide. J. Am. Chem. Soc. 1958, 80, 1339.
(11) Yang, K.; Zhang, S.; Zhang, G.; Sun, X.; Shuit-Tong Lee, S-T.; Liu, Z. Graphene in Mice: Ultrahigh In Vivo Tumor Uptake and Efficient Photothermal Therapy, Nano Lett. 2010, DOI: 10.1021/nl100996u.Yang Example 2. Production of Nanoparticle Catalysts Supported on Graphene by Laser Irradiation of Solids and Solutions In addition to the unique electronic properties of graphene, other properties such as high thermal, chemical and mechanical stability as well as high surface area also represent desirable characteristics as 2-D support layers for metallic and bimetallic nanoparticles in heterogeneous catalysis. Recent advances in the production of graphene sheets through the reduction of exfoliated graphite oxide (GO) have provided efficient approaches for the large scale production of chemically converted graphene (CCG) sheets which can be readily used as a catalyst support. The large surface area (2600 $m^2g^{-1}$, theoretical value) of graphene and high thermal and chemical stability provide excellent catalyst support. Although several methods have been reported for the synthesis of metal-GO and metal-graphene nanocomposites, most of the approaches involve the use of chemical reducing agents, and there are only a few reports on the photocatalytic reduction of GO using photocatalysts such as $TiO_2$[1], $ZnO$[2], $BiVO_4$[3], and polyoxometlate[4]. The main advantage of using photochemical and photothermal reduction methods to prepare metal nanoparticles supported on graphene is to avoid the use of toxic chemical reducing agents thus providing a green approach for the synthesis and processing of metal-graphene nanocomposites. Also for applications in catalysis, it is desirable to completely remove any trace reducing or capping agents from the surface of the supported nanocatalysts since these organic species tend to significantly reduce the catalytic activity and poison the nanoparticle catalysts. Other advantages include better control of the reduction processes without the need of high temperatures, and the possibility of reducing two or more different metal ions on the graphene surface which could produce graphene nanocomposites with interesting catalytic, magnetic and optical properties.

Although fully oxidized GO is an insulator, partially oxidized GO has semiconductor properties with a bandgap that is determined by the extent of oxygenation of graphite.[5-7] This is due to the local changes in the carbon hybridization from $sp^2$ to $sp^3$ as oxidation of graphite sheets takes place. Bandgap energies between 2.5-4.0 eV have been calculated for a O/C ratio >0.5.42. The previous Example describes a facile laser reduction method for the synthesis of Laser Converted Graphene (LCG) from GO, and the first direct measurements of the temperature rise in water resulting from the photothermal deoxygenation of GO. Absorption of a single 355 nm photon (3.5 eV) or two 532 nm photons by GO excites valence-to-conduction transitions (2.3 eV) which generates electron-hole pairs within the semiconductor GO followed by non-radiative recombination which results in efficient energy conversion. Since electron-lattice temperature equilibrium occurs on the picosecond time scale, the resulting thermal energy is sufficient for the rapid removal of $O_2$, $CO$, $CO_2$ and $H_2O$ from GO thus forming deoxygenated GO (or reduced GO). In addition to the photothermal effects, the generation of electron-hole pairs in GO in the presence of a hole scavenger molecule such as alcohol or glycol should be highly efficient to activate the reduction of GO. Furthermore, in the presence of metal ions, simultaneous reduction of the GO and metal ions should take place thus generating metal-graphene nanocomposites. This example describes our findings regarding the laser photoreduction of GO and the metal ions and the formation of metal-graphene nanocomposites. First, we demonstrate that GO can be reduced by the 532 nm laser irradiation in the presence of a reducing environment such as ethanol-water or PEG-water mixtures much more efficiently than in pure water. Second, we demonstrate that gold and silver ions can be reduced in the presence of GO, and then we compare the efficiency of the metal ion-GO simultaneous reduction processes in different solvent environments namely ethanol-water, PEG-water and pure water. Third, we evaluate the photothermal effects associated the photocatalytic reduction of the metal ions in the presence of GO. Fourth, we demonstrate that similar reduction processes of GO and gold ions can take place using a tungsten-halogen lamp instead of a pulsed laser source thus providing a rationale for using solar energy for photocatalytic reduction of metal ions in the presence of GO. Finally, we provide plausible mechanisms for the laser photoreduction and photothermal effects in different solvent environments.

Experimental Section

In the experiments, GO was prepared by the oxidation of high purity graphite powder (99.9999%, 200 mesh, Alfa Aesar) according to the method of Hummers and Offeman.[8] After repeated washing of the resulting yellowish-brown cake with hot water, the powder was dried at room temperature under vacuum overnight. 2 mg of the dried GO was sonicated in 10 mL of deionized water (or 50% ethanol-water or 2% PEG-water mixture) until a homogeneous yellow dispersion was obtained. For the reduction of GO alone, 3 mL of the GO solution was irradiated with a pulsed Nd:YAG laser (unfocused, 2nd harmonic $\lambda$=532 nm, h$\nu$=2.32 eV, pulse width $\tau$=7 ns, repetition rate=30 Hz, fluence ~0.1 J/cm2, Spectra Physics LAB-170-30) under continuous stirring. For the Au-GO experiments, hydrogen tetrachloroaurate(III) trihydrate ($HAuCl_4 \cdot 3H_2O$, Sigma Aldrich, 30 Wt % Au(III) chloride solution in dilute HCl, with purity of 99.99%) was added to the GO solutions according the amounts specified in the figure captions of the data. For the Ag nanoparticles, 25 mg of $AgNO_3$ (99.99%, Sigma-Aldrich) were added to 3 mL GO (2 mg/10 mL) solutions before the laser irradiation experiments.

The tungsten-halogen lamp used was 500 W. The distance between center of the sample and light source was 35 cm and no filters were used. The temperature of the solution was monitored during irradiation using a thermocouple immersed in the solution.

The LCG sheets and the metal-LCG nanocomposites were separated and dried overnight under vacuum before the XRD or the XPS measurements. TEM images were obtained using a Joel JEM-1230 electron microscope operated at 120 kV equipped with a Gatan UltraScan 4000SP 4K×4K CCD camera. Absorption spectra were recorded using a Hewlett-Packard HP-8453 diode array spectrophotometer. The X-ray diffraction patterns were measured with an X'Pert Philips Materials Research Diffractometer using Cu K$\alpha$1 radiation. The X-ray photoelectron spectroscopy (XPS) analysis was performed on a Thermo Fisher Scientific ESCALAB 250 using a monochromatic Al KR.

Results and Discussion

1. Laser Assisted Photoreduction of GO in Different Solvents

XRD data of the LCG obtained after the 532 nm (4 W, 30 Hz) irradiation of GO for 10 min in different solvents was obtained. The XRD pattern of the exfoliated GO is characterized by a peak at 2$\theta$=10.9° corresponding to a d-spacing of 8.14 Å resulting from the insertion of hydroxyl and epoxy groups between the graphite sheets as a result of the oxidation process of graphite. Following the 532 nm laser irradiation for a few minutes, the yellow golden color of the GO solution changes to black with complete disappearance of the XRD 10.9° peak (FIG. 5), thus indicating the reduction of GO and the restoration of the $sp^2$ carbon sites in the LCG. The irradiation time required for the reduction of GO varies from a few to several minutes depending on the nature of the solvent, the laser power, the concentration of GO and the volume of the solution. For example, under identical conditions of GO concentration (0.2 mg/mL), solution volume (3 mL) and laser power (4 W, 30 Hz), the reduction of GO is completed after 5, 8, and 10 min in 50% ethanol-water, 2% PEG-water and pure water, respectively.

FT-IR spectra of GO and the LCG following the 532 nm (4 W, 30 Hz) irradiation for 10 min in 50% ethanol-water, 2% PEG-water and pure water showed strong bands corresponding to the C=O stretching vibrations of the COOH groups at 1740 $cm^{-1}$, the O—H deformations of the C—OH groups at 1350-1390 $cm^{-1}$, the C—O stretching vibrations at 1060-1100 $cm^{-1}$, and the epoxide groups (1230 $cm^{-1}$). These bands are almost completely absent from the spectrum of the LCG thus confirming the conversion of GO into graphene following the 532 nm laser irradiation.

The UV-Vis spectrum of GO is characterized by significant absorption below 400 nm with a characteristic shoulder at 305 nm attributed to n→$\pi$* transitions of C=O bonds. Without being bound by theory, with the 532 nm laser irradiation, two photon absorption is expected to contribute significantly to the absorption of the laser energy by GO due to excited state nonlinearities which enhance the two-photon absorption of GO at 532 nm in the nanosecond regime. UV-Vis spectra of GO following the 532 nm laser irradiation in 50% ethanol-water and 2% PEG-water mixtures, and in pure water showed that, in all cases, the characteristic shoulder of GO at 305 nm disappears after laser irradiation, and the absorption peak of GO at 230 nm redshifts to about 270 nm due to the $\pi$→$\pi$* transitions of extended aromatic C—C bonds as the electronic conjugation within graphene is restored in the LCG.

The XPS C1s spectrum of GO shows peaks corresponding to oxygen-containing groups between 285.5 and 289 eV, in addition to the $sp^2$-bonded carbon C=C at 284.5 eV. Typically, peaks at 285.6, 286.7, 287.7 and 289 are assigned to the C1s of the C—OH, C—O, C=O, and HO—C=O groups, respectively. The XPS data of the LCG in 50% ethanol-water, 2% PEG-water, and pure water clearly indicate that most of the oxygen-containing groups in GO are removed after the laser irradiation. The TEM images of the reduced GO showed wrinkled and partially folded sheets with a lateral dimension of up to a few microns in length. No obvious differences were observed in the TEM images of the LCG in different solvent environments.

As indicated above, the reduction of GO in the presence of ethanol or PEG is much faster than in pure water under identical solution volume, concentration and laser power conditions. For example, 532 nm irradiation with 1 W laser power (30 Hz) converts GO in pure water into graphene in about 40 min (7.2×$10^3$ laser pulses), while in the presence of 50% ethanol or 2% PEG, the same concentration of GO can be reduced in about 22, or 32 min, respectively. Obviously, the ethanol and PEG solutions exhibit higher reduction efficiencies than pure water. Without being bound by theory, this is attributed to the role of ethanol or PEG in scavenging the holes generated by the laser irradiation of GO. Following the absorption of two photons by GO and the generation of electron-hole (e-h) pairs, the holes are scavenged by ethanol or PEG thus leaving the photogenerated electrons to reduce GO. It is likely that mutual photocatalytic reduction between different GO sheets occurs at the early stages of the photocatalytic reaction. However, in pure water in the absence of hole scavengers, photothermal energy conversion appears to be the dominant mechanism leading to the deoxygenation of GO. Therefore, the mechanism involved in the laser reduction of GO in solution could involve contributions from both electron and thermal processes depending on the nature of the solvent. The contributions of both processes to the simultaneous reduction of GO and metal ions are presented and discussed in the next section.

2. Photoreduction of Gold Ions and GO in Different Solvents

Figure 6A:
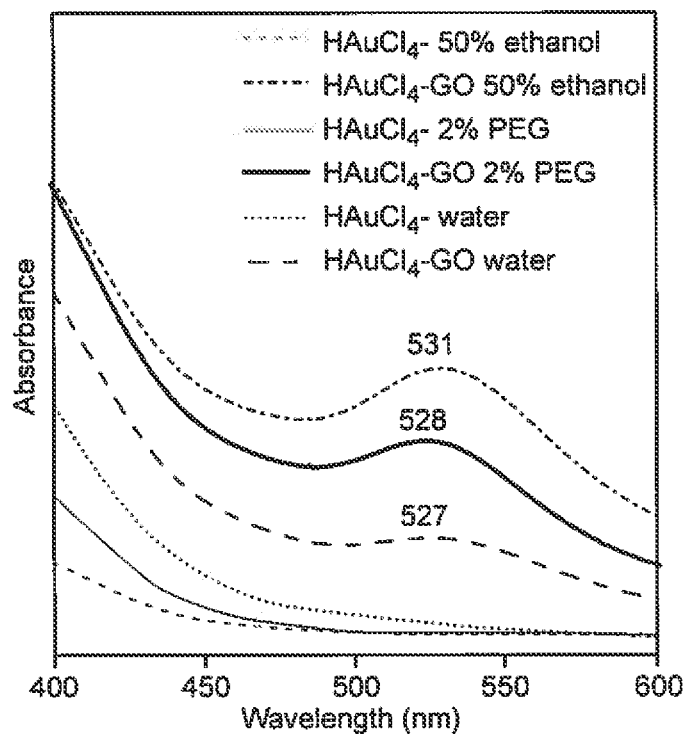
FIGS. 6A and B. A, Absorption spectra of 25 μL $HAuCl_4$+ GO in 50% ethanol-water, 2% PEG-water and pure water recorded after two minutes laser irradiation (532 nm, 4 W, 30 Hz). Dotted lines represent data of bank solutions containing the same amount of $HAuCl_4$ but no GO under identical laser irradiation conditions. B, Absorption spectra of the same solutions in (a) irradiated with lower laser power (532 nm, 1 W, 30 Hz) showing no formation of gold nanoparticles in the pure water solution (black).

FIG. 6A compares the absorption spectra of GO solutions containing the same amount of $HAuCl_4$ in 50% ethanol-water and 2% PEG-water mixtures and in pure water before and after the 532 nm irradiation (4 W, 30 Hz) for 2 min. The reduction of the gold ions and formation of Au nanoparticles is clearly evident by the observation of the Surface Plasmon Resonance (SPR) band of Au nanoparticles (527-531 nm) as shown. It is clear that laser excitation of GO is involved in the reduction of the Au ions since irradiation of the $HAuCl_4$ solutions in the absence of GO under identical conditions does not result in the formation of Au nanoparticles (FIG. 5). In the three solvent systems, an increase in the SPR band intensity of the Au nanoparticles with increasing the laser irradiation time from 2 to 10 min was observed (not shown) thus providing direct evidence for increasing the nanoparticles' concentration with the number of photons absorbed by GO. This confirms that the reduction of the Au ions is directly coupled with the absorption of the 532 nm photons by GO. Furthermore, the SPR band of Au nanoparticles shows a systematic red shift with irradiation time indicating the formation of larger or aggregated Au nanoparticles at longer irradiation times (not shown). For example, the SPR band shifts from 531 nm after 2 min irradiation to 548 nm after 6 min irradiation of GO in the 50% ethanol-water mixture (not shown). Similarly, the SPR band shifts from 535 nm to 558 nm after 2 min and 10 min irradiation times, respectively of GO in the 2% PEG-water mixture (not shown). The redshift in the SPR band is attributed to the formation of large aggregated Au nanoparticles as confirmed by the TEM images showing the presence of particles in the size range of 30-70 nm after 10 min irradiation (not shown). These large particles are formed via an Ostwald ripening process where the initially formed small particles with higher surface energies are consumed in the growth of the large particles with lower surface energies at longer irradiation times. Selective formation of small Au nanoparticles can be achieved by decreasing the concentration of $HAuCl_4$ and using shorter irradiation times where the Ostwald ripening process can be minimized.

Figure 6B:
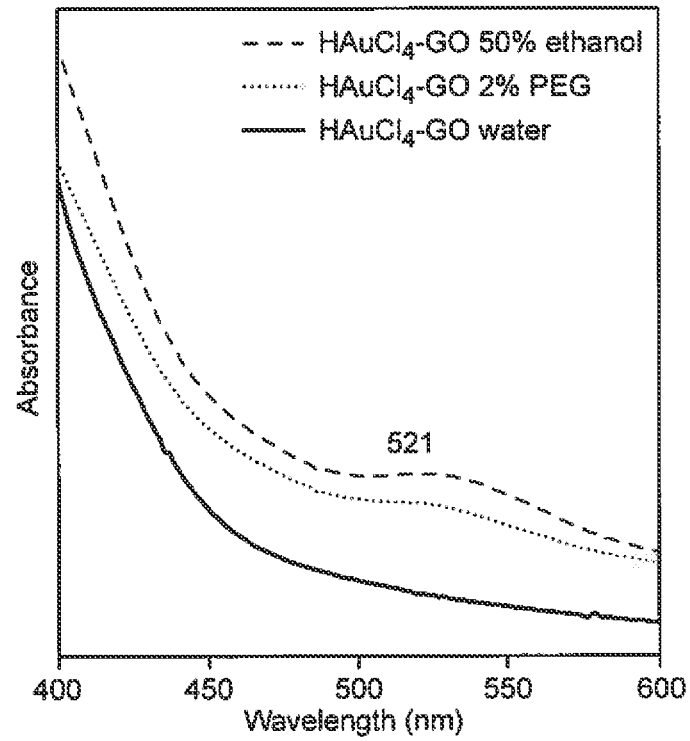

The increase in the SPR band intensity of the Au nanoparticles for the 50% ethanol and the 2% PEG solutions as compared to pure water is attributed to increasing the concentration of the Au nanoparticles in the presence of ethanol or PEG consistent with the increased reduction efficiencies of these solutions over pure water. At low laser power (1 W, 30 Hz), the reduction of the Au ions is not observed in pure water as indicated by the absence of the SPR band of Au nanoparticles as shown in FIG. 6B. This suggests that the laser reduction mechanism is different in water than in the presence of alcohol or PEG.

TEM images were obtained of the Au nanoparticles dispersed on the surface of the LCG graphene sheets formed by the 2 min laser irradiation of the GO solutions containing the same amount of $HAuCl_4$ in 50% ethanol-water and 2% PEG-water mixtures and in pure water. From the images, it was clear that the concentration of the Au nanoparticles formed in the GO-water solution is significantly lower than the concentration formed in the presence of ethanol or PEG. Again, this is likely a consequence of the favorable reducing environment created by ethanol or PEG as compared to water.

The XRD patterns of GO before and after laser irradiation in the presence of $HAuCl_4$ in the 50% ethanol-water mixture show the disappearance of the characteristic diffraction peak of GO at $2\theta=10.9°$ as shown in FIG. 7A. However, irradiation of GO in water in the presence of $HAuCl_4$ shows that a small GO peak remains in the XRD suggesting that only a partial reduction of GO takes place. On the other hand, the XRD pattern of Au is clearly observed in the resulting Au-LCG nanocomposites formed by laser irradiation of the GO solutions containing the same amount of $HAuCl_4$ as shown in FIG. 7B. We observe a systematic decrease in the extent of deoxygenation of GO by the 532 nm irradiation as the concentration of $HAuCl_4$ in the GO solution increases as evident by the increase in the intensity of the XRD peak of GO at $2\theta=10.9°$ as shown in FIG. 7C. However, in the absence of $HAuCl_4$, 532 nm irradiation of GO in water results in complete disappearance of the XRD peak of GO as shown in FIG. 5. This indicates that in the 532 nm irradiation of the $HAuCl_4$-GO solution, the resulting Au nanoparticles are supported on partially reduced GO. FIG. 7D shows the dependence of the reaction on the concentration of $HAuCl_4$.

To probe the extent of GO reduction in the presence of Au nanoparticles, we compared the C1s XPS spectra of GO before and after laser irradiation in the presence of $HAuCl_4$ in the 50% ethanol-water, 2% PEG-water and in pure water solutions as shown in FIG. 8A. In the three solvent systems, the C1s XPS spectra indicate that only partial reduction of GO takes place as evident by the presence of the XPS C1s peaks corresponding to C—O and possibly C=O groups. On the other hand, the reduction of the Au ions is clearly confirmed by the observation of the doublet corresponding to the $4f^{5/2}$ (87.8 eV) and $4f^{7/2}$ (84.2 eV) of $Au^0$ as shown in FIG. 8B.

The partial reduction of GO in the presence of the Au ions is attributed to the formation of Au nanoparticles which efficiently absorb the 532 nm photons due to the SPR (~530 nm) thus decreasing the probability of two-photon absorption by GO. This will result in decreasing both the number of the photogenerated electrons needed for the reduction of GO as well as the photothermal energy conversion resulting from the nonradiative recombination of the electron-hole pairs. To confirm this point we compare the above results involving irradiation of GO in the presence of Au ions with the reduction of GO in the presence of Ag ions as presented in the next section.

3. Photoreduction of Silver Ions and GO in Different Solvents

Similar to the formation of Au nanoparticles, irradiation of GO in water by the 532 nm laser in the presence of $AgNO_3$ results in the formation of Ag nanoparticles. This is evident from the observation of the SPR band of Ag nanoparticles ~420 nm shown in FIG. 9A, and the TEM images of the reduced graphene oxide-containing Ag nanoparticles. The XRD patterns of GO before and after laser irradiation in the presence of $AgNO_3$ in the 50% ethanol-water mixture as well as in pure water show the disappearance of the GO peak at $2\theta=10.9°$ as shown in FIG. 9B. This result is different from the $Au^{3+}$ experiments where only partial reduction of GO was observed as indicated by the incomplete disappearance of the GO diffraction peak following the irradiation of the $HAuCl_4$-GO solution. Furthermore, the XPS spectra of the Ag-graphene nanocomposites prepared in 50% ethanol-water and in pure water clearly indicate that most of the oxygen-containing groups in GO have been removed after laser irradiation as shown in FIG. 9D. Again, the XPS C1s spectra of the Ag-graphene nanocomposites (FIG. 9D) is very different from the corresponding data of the Au-partially reduced graphene oxide shown in Figure SA. Therefore, it appears that the partial reduction of GO in the presence of the Au ions is indeed due to the absorption of the 532 nm photons by the Au nanoparticles which competes with the two photon absorption by GO required for the creation of electron-hole pairs in GO.

4. Photothermal Effects of Laser Irradiated $Au^{3+}$/GO and $Ag^+$/GO Solutions To shed more light on the mechanisms involved in the reduction of GO in the presence of metal ions, we measured the temperature rise of the $Au^{3+}$/GO and $Ag^+$/GO solutions in the 50% ethanol-water, the 2% PEG-water mixtures and in pure water during the 532 nm laser irradiation. The results for the 50% ethanol-water mixture are shown in FIG. 10.

The temperature rise reflects the steady state net heat transfer to the solution following the nonradiative recombination of the e-h pairs in GO. It is clear that laser irradiation of the metal ions' solutions in the absence of GO does not show any significant temperature rise under identical conditions as shown in FIG. 10. Therefore, it can be concluded that the temperature rise of the GO solutions containing metal ions following the 532 nm irradiation is mainly due to the photothermal energy conversion by GO and the LCG. Also, the SPR bands of Au and Ag are not observed in the UV-Vis spectra of the laser irradiated HAuCl4 and $AgNO_3$ solutions in the absence of GO. Therefore, the reduction of the metal ions appears to be coupled to the absorption of the 532 nm photons by GO and the subsequent photogenerated electron or photothermal reduction processes depending on the nature of the solvent. A decrease in the temperature rise of the GO solution containing metal ions is observed as compared to the GO solution without the metal ions as shown in FIG. 10. Similar trends have been observed for the Au and Ag ions in the GO solutions of 2% PEG-water and pure water (not shown). It is reasonable to assume that the decrease in the temperature rise of the irradiated solution in the presence of GO-metal ions mixture is qualitatively related to the contribution of the photothermal effects to the reduction mechanism of the metal ions and GO. In other words, the energy required for reduction of the metal ions is provided by the photothermal energy conversion of GO and therefore the net amount of heat transferred to the solution is decreased. However, since the photothermal effects appear to be similar in 50% ethanol-water, 2% PEG-water and in pure water, the enhancement of the reduction of GO and metal ions in ethanol and PEG is most likely due to hole scavenging properties of these solvents which leave the photogenerated electrons available for the reduction of the metal ions and GO.

To investigate the stability of the Au nanoparticles deposited on the partially reduced GO, repeated 532 nm irradiation cycles (5 min irradiation time at 30 Hz) were performed on the same $HAuCl_4$-GO solution. In each cycle, the solution was allowed to cool down to room temperature after the laser had been turned off. We found that the color of the solution changes from red during the first irradiation cycle (indicating the formation of the Au nanoparticles), to dark red to violet to blue with successive irradiation cycles. The temperature rise of the solution increases slightly after each cycle for a number of cycles that depends on the laser power, and then the temperature falls below the value corresponding to the first cycle. FIG. 11A shows the temperature profiles of repeated irradiation cycles of the $HAuCl_4$-GO solution using a 2 W average laser power. After each cycle, the solution was cooled down before starting the next irradiation cycle. In the $7^{th}$ cycle, irradiation starts when the temperature of the solution was 36° C. and it became 47° C. after irradiation for 10 min. Then the solution was cooled down to room temperature and the $8^{th}$ cycle started for 10 min where the temperature reached only 41° C., and the solution color changes to dark blue. This suggests that the drop in temperature is associated with the formation of large aggregated Au nanoparticles. The formation of large aggregates of Au nanoparticles after repeated laser irradiation cycles is clearly evident from the observed red shift of the SPR band of the Au nanoparticles from 530 nm after the 2nd irradiation cycle (2 W, 30 Hz) to 546 nm after the 6th cycle as shown in FIG. 11B. After the deactivating 8th cycle, a significant decrease in the SPR band intensity is also observed accompanied by a strong red shift to 557 nm with the appearance of a broad continuum absorption extended to 900 nm (FIG. 11B). These results indicate that the deactivation of the photothermal effect of the Au nanoparticles-GO system is attributed to the formation of large aggregates which absorb more toward the red but without well-defined SPR bands.

5. Photoreduction Using Tungsten-Halogen Lamp

Figure 12:
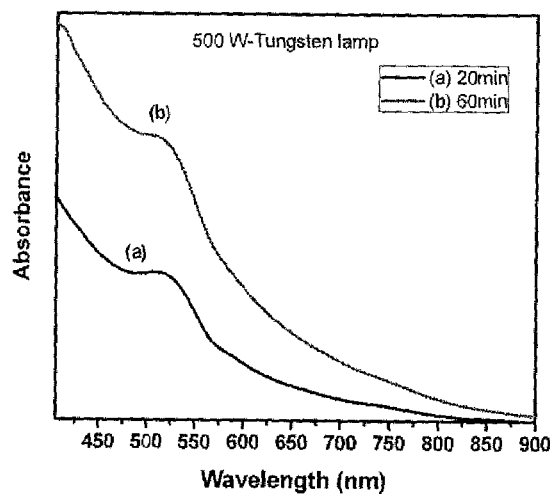
FIG. 12. Absorption spectra of 10 μL HAuCl$_4$+GO (1 mg in 10 mL water) recorded after 20 and 60 minutes irradiation with the tungsten-halogen lamp (500 W). The distance between center of the sample and light source was 25 cm and no filters were used.

To explore the application of solar energy for the photochemical reduction of GO and gold ions, we used a 500 W tungsten-halogen lamp as a model for the solar energy. Irradiation of a 10 mL GO solution containing 10 µL $HAuCl_4$ results in the formation of Au nanoparticles within a few minutes as evident by the observation of the SPR band at 530 nm (FIG. 12) and the TEM images of Au nanoparticles formed on the GO sheets after 20 irradiations of the $HAuCl_4$+GO solutions in water, 10% ethanol and pure ethanol, under identical conditions (not shown). Similar to the laser irradiation experiments, no Au nanoparticles are formed when the $HAuCl_4$ aqueous solution is irradiated in the absence of GO, thus confirming that the Au ions are reduced via the absorption of photons by GO. Furthermore, the reduction of the Au ions is much more efficient and faster in the presence of ethanol consistent with the 532 nm laser irradiation results. Therefore, the main features of the photocatalytic reduction of GO and metal ions observed using pulse laser irradiation are reproduced by using the tungsten-halogen lamp. This demonstrates the possibility of using solar energy for the photoreduction of metal ions-GO mixtures and the formation of metal-graphene nanocomposites.

6. Mechanisms of Photoreduction and Photothermal Effects

The reduction mechanism of the metal ions ($M^+$) probably involves the participation of electrons from the LCG or the partially reduced GO. As discussed above, GO as a semiconductor absorbs either two photons of 532 nm or one photon of 355 nm resulting in the creation of an $e^-$-$h+$ pair. In the presence of a reducing environment provided by ethanol or PEG, the holes are scavenged to produce protons and reducing organic radicals. The electrons are used for the reduction of the metal ions, and since the alcohol radicals ($C_2H_4OH$) are strong reducing agents they undergo oxidation to $CH_3CHO$ and therefore reduce GO. The possible mechanism can be summarized as follows:

$$GO + hv \rightarrow GO(h+ + e-) \qquad (1)$$

$$h^+ + C_2H_5OH \rightarrow C_2H_4OH + H^+ \qquad (2)$$

$$M^+ + GO(e-) \rightarrow GO + M \qquad (3)$$

$$nC_2H_4OH + GO \rightarrow RGO + nCH_3CHO + nH^+ \qquad (4)$$

In the absence of a reducing environment as in pure water, photothermal energy conversion becomes the major mechanism for the reduction of GO and the metal ions which is a less efficient mechanism than the photochemical reduction in a reducing environment. This is consistent with the higher laser power needed for the reduction of the metal ions and GO in the absence of a reducing solvent. The partial reduction of GO observed in the presence of Au ions suggests that the reduction of the Au ions takes place very rapidly and since the resulting Au nanoparticles absorb the 532 nm photons much more efficiently than GO, the photothermal energy conversion by GO is decreased and complete reduction of GO is not possible.

SUMMARY

In summary, we have demonstrated the photocatalytic reduction of gold and silver ions by GO using both laser and tungsten lamp irradiation in different solvent environments. The mechanism operating in the laser reduction of GO in solution involves contributions from both electron and thermal processes depending on the nature of the solvent. The gold and silver ions are efficiently reduced following the laser or the tungsten lamp irradiation for a few minutes in water-ethanol, water-PEG or pure water solvents. The reduction of GO in the presence of ethanol or PEG is much faster than in pure water under identical experimental conditions. This is attributed to the role of ethanol or PEG in scavenging the holes generated by the irradiation of GO thus leaving the photogenerated electrons to reduce GO. In the absence of a reducing environment as in pure water, photothermal energy conversion becomes the major mechanism for the reduction of GO and the metal ions which is a less efficient mechanism than the photochemical reduction in a reducing environment. Partial reduction of GO occurs with the 532 nm laser irradiation in the presence of Au3+ ions due to the efficient absorption of the 532 nm photons by the Au nanoparticles which competes with the two-photon excitation of GO.

The present approach leads to the formation of metal nanocrystals dispersed on the reduced or partially reduced GO surfaces without the use of chemical reducing or capping agents which tend to significantly reduce the catalytic activity and poison the nanoparticle catalysts. The observed photothermal effects leading to a significant increase in the temperature of the solution suggests that metal-graphene nanocomposites could be promising materials for the efficient conversion of solar energy into usable heat for a variety of thermal, thermochemical and thermomechanical applications.

REFERENCES FOR EXAMPLE 2

1. Williams, G.; Seger, B.; Kamat, P. V. ACS Nano 2008, 2, 1487-1491.
2. Williams, G.; Seger, B.; Kamat, P. V. Langmuir 2009, 25, 13869-13973.
3. Ng, Y. H.; Iwase, A.; Kudo, A.; Amal, R. J. Phys. Chem. Lett. 2010, 1, 2607-2612,
4. Li, H.; Pang, S.; Feng, X.; Mullen, K.; Bubeck, C. Chem. Commun. 2010, 46, 6243-6245.
5. Ito, J.; Nakamura, J.; Natori, A. J. Appl. Phys. 2008, 103, 113712.
6. Yan, J. A.; Xian, L.; Chou, M. Y. Phys. Rev. Lett. 2009, 103, 086802.
7. Lahaye, R. J. W. E.; Jeong, H. K.; Park, C. Y.; Lee, Y. H. Phys. Rev. B. 2009, 79, 125435.
8. Hummers, W. S., Jr.; Offeman, R. E. J. Am. Chem. Soc. 1958, 80, 1339-1339.

Example 3. Photothermal Energy Conversion by Metal and Semiconductor Nanoparticle Composites of Graphite Oxide and Graphene in Water Using Lasers and Tungsten-Halogen Lamps This Example describes a method for the conversion of sunlight and other visible, infrared and ultraviolet radiation into thermal energy which can be used for heating water for domestic use as well as for the evaporation of sea water for efficient desalination. The invention uses graphite oxide and graphene as well as their metal and semiconductor nanocomposites such gold nanoparticles-graphene oxide nanocomposites, gold nanoparticles-graphene nanocomposites, and silicon-graphite oxide, and silicon-graphene nanocomposites. Other metal nanoparticles used with graphite oxide and graphene are silver, palladium, copper, and platinum. Other semiconductor nanoparticles used with graphite oxide and graphene are titanium dioxide and zinc oxide.

To demonstrate the enhanced photothermally activated reduction of metal ions by GO in water, Au, Ag and Pd nanoparticles supported on graphene were synthesized by the 532 nm laser irradiation of GO solutions containing $AuCl_3$ in HCl, $AgNO_3$ and $Pd(NO_3)_2$, respectively. The reduction of the metal ions is clearly evident by the observation of the corresponding SPR (surface plasmon resonance) bands for Au and Ag (~530 nm and 420 nm, respectively), and XRD data of the metal nanoparticles deposited on the LCG as shown in FIG. 13. TEM images confirmed these findings.

The formation of the Au nanoparticles appears to compete with the conversion of GO to graphene by the 532 nm irradiation. The systematic decrease in the extent of deoxygenation of GO by the 532 nm radiation as the concentration of the gold precursor in the GO solution increases is clearly evident in the XRD data presented in FIG. 7C, and described in the previous example. It is clear that as the concentration of the Au precursor increases, the intensity of XRD peak characteristic of GO increases. This is accompanied by an increase in the intensity of SPR of Au at 530 nm as the concentration of Au precursor increases as shown in FIG. 7D (previous example). It is also clear that the strong plasmon absorption of the 532 nm photons by the gold nanoparticles results in less photothermal energy available for the deoxygenation of GO. This indicates that the resulting Au nanoparticles are supported on GO or a mixture of GO and graphene.

Figure 14:
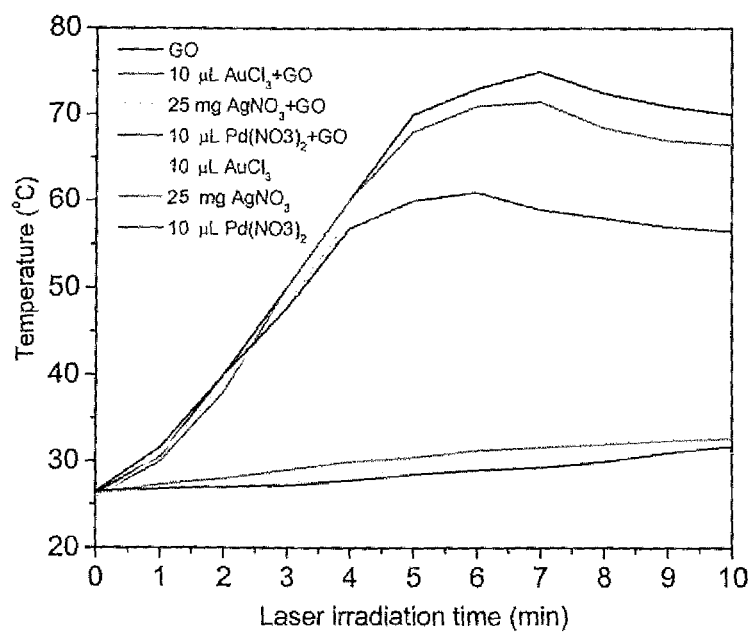
FIG. 14. Temperature changes during laser irradiation (532 nm, 5 W, 30 Hz) of graphite oxide (GO) solutions (3 ml solution, 2 mg GO/10 mo H$_2$O) containing AuCl$_3$, AgNO$_3$, and Pd(NO3)$_2$. Comparisons with the same solutions but without GO are also shown.

The temperature changes caused by the photothermal energy conversion of GO in the presence of metal ions (FIG. 14) indicate that energy required for the reduction of the metal ions is provided by the photothermal energy conversion. It is clear that laser irradiation of the $AuCl_3$/HCl and $AgNO_3$ solutions in absence of GO does not result in the formation of Au or Ag nanoparticles, respectively. FIG. 14 also shows that no temperature rise is observed during the laser irradiation of these solutions. Accordingly, the SPR bands of Au and Ag are not observed in the UV-Vis spectra of the laser irradiated $AuCl_3$/HCl and $AgNO_3$ solutions in the absence of GO.

Figure 15:
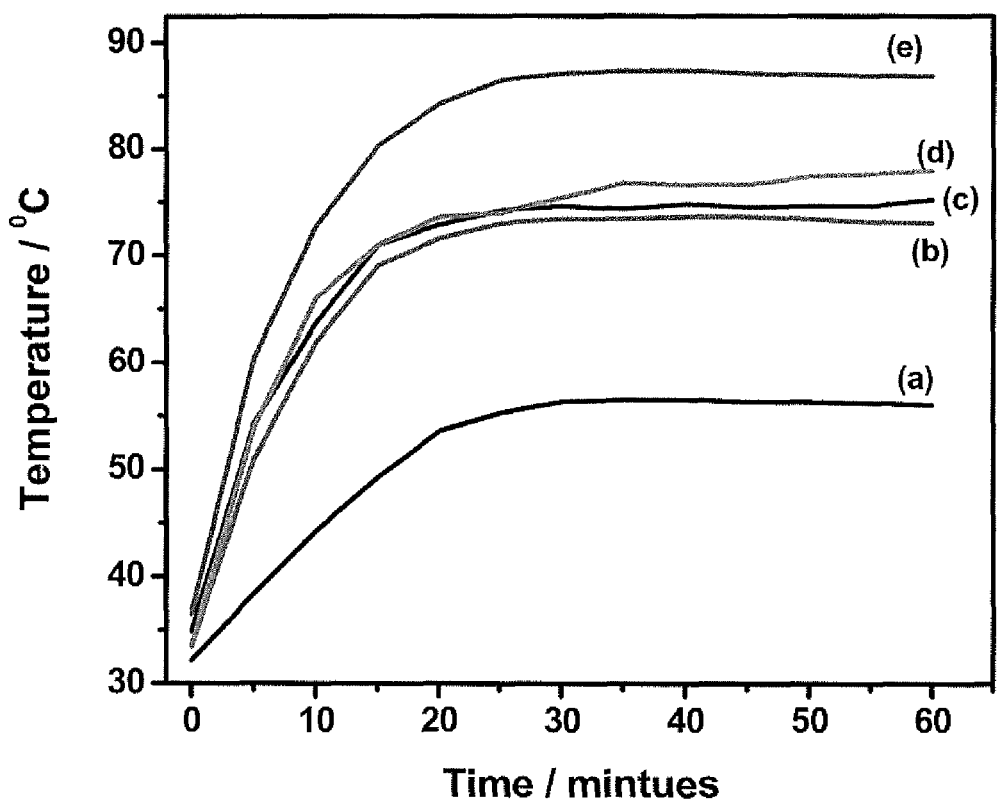
FIG. 15. Photothermal effects of gold nanospheres, GO and their mixture compared to water.

FIG. 15 shows the temperature increase in solutions of (a) pure water; (b), 1 ml Au particles+9 ml water; (c) 10 ml of water with 1 mg of suspended GO; (d), 10 ml of water with 1 mg of suspended GO+10 μl of $HAuCl_4$/HCl; (e) mixture contains 1 ml of gold spheres and 9 ml of GO mixture, in response to irradiation of the solutions with energy from a tungsten-halogen lamp (500 W).

Figure 16A:
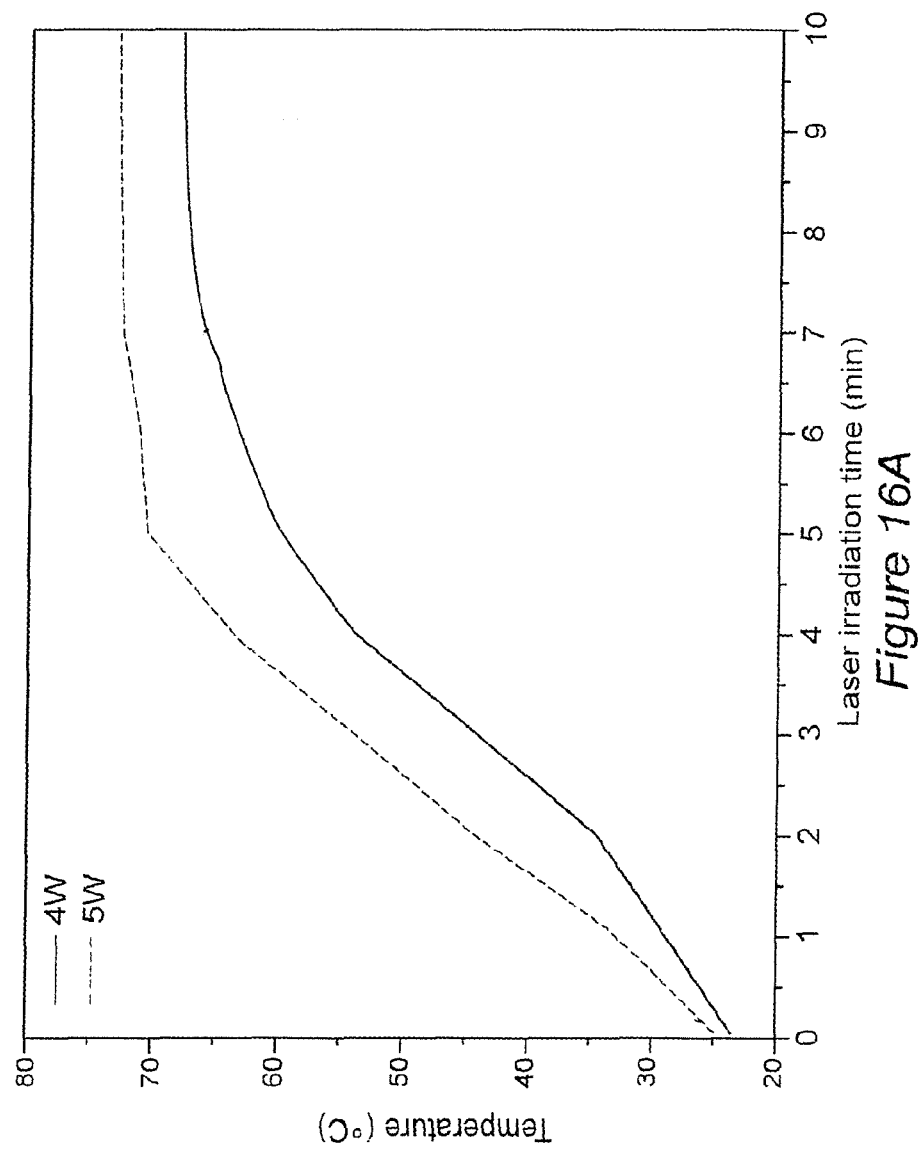
FIGS. 16A and B. A, Temperature changes during laser irradiation (532 nm, 4 and 5 W, 30 Hz) of graphite oxide (GO) solutions (3 ml solution, 2 mg GO/10 ml H$_2$O) containing 1 mg Si nanoparticles; B, Temperature changes during laser irradiation (532 nm, 5 W, 30 Hz) of graphite oxide (GO) solutions (3 ml solution, 2 mg GO/10 ml H$_2$O) containing 1 mg Si nanoparticles.
Figure 16B:
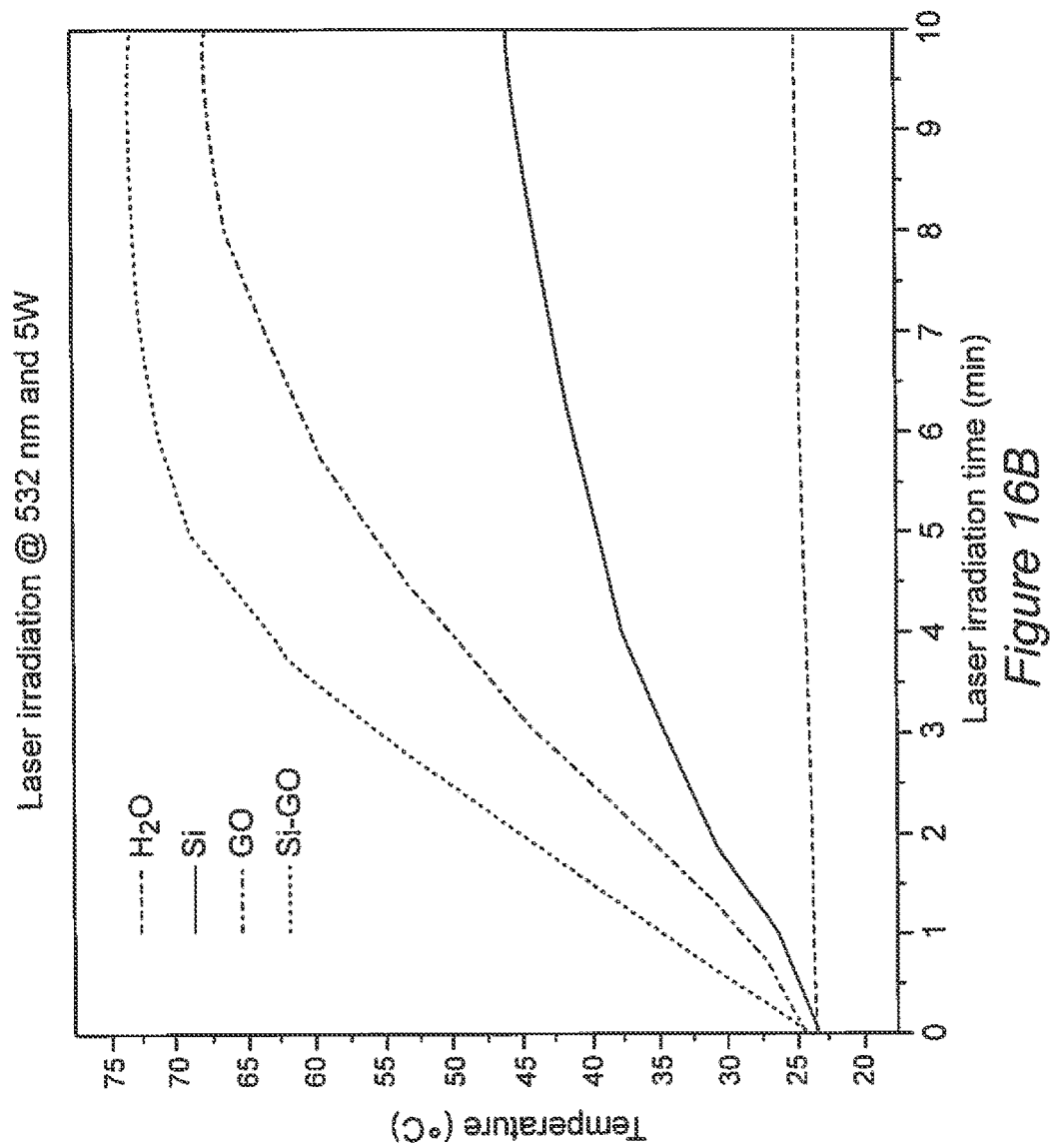
Figure 19:
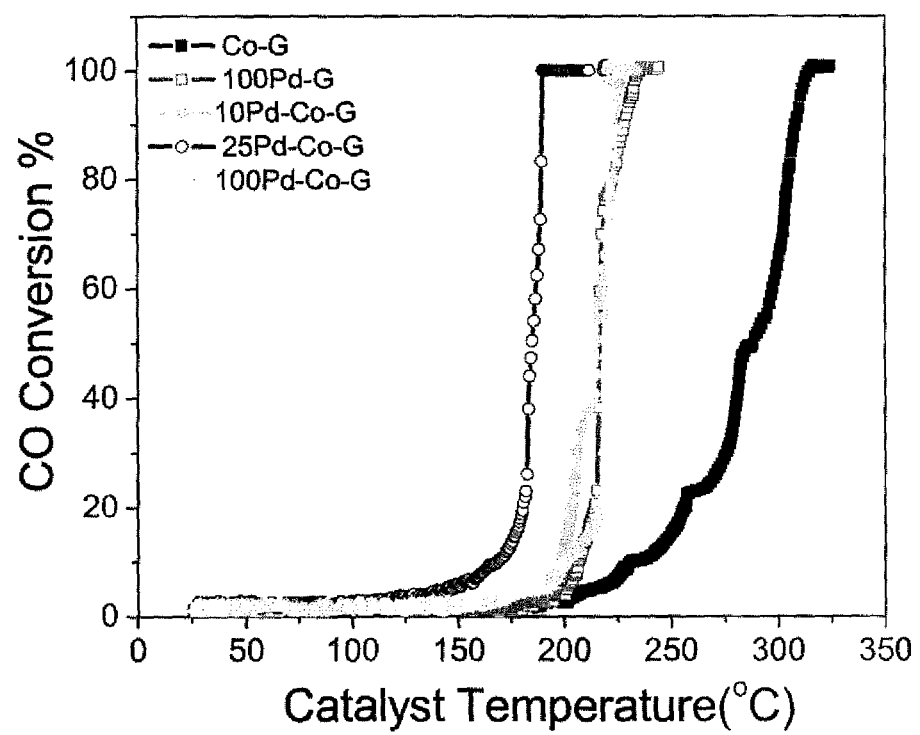
FIG. 19. Catalytic oxidation of CO on bimetallic PdCo nanoparticles supported on graphene.

FIGS. 16A and B show the efficient coupling of photothermal energy conversion via laser irradiation of GO solutions containing silicon nanoparticles.

Example 4. Laser Synthesis of Bimetallic Nanoparticles Supported on Graphene Bimetallic PdCo nanoparticles supported on graphene are prepared by the laser irradiation process in solutions and the resulting PdCO nanoparticles exhibit higher catalytic activity for CO oxidation as compared to Pd/graphene and Co/graphene catalysts made from Pd nanoparticles or Co nanoparticles supported on graphene, as shown in the data presented in FIGS. 17A-C, 18A and B and 19.

Example 5. Improved Solar Thermal Energy Conversion Processes

Solar thermal technology has been used for centuries to provide water heating and/or steam for many purposes. The most common uses are: domestic water heating; and commercial applications in order to provide larger quantities of hot water for use in hotels, hospitals, and restaurants. Additional uses include solar crop drying technologies, basic solar stills to purify water in remote regions where contaminated water cannot be avoided, solar-driven desalination and solar thermal processed steam for industrial purposes. In the latter example, processed steam can be used for different industrial applications based on its ultimate temperature.

A solar steam boiler can produce steam at temperatures up to 150° C. and can thus replace the low pressure steam boilers currently used in the textile, chemical, and food industries. A solar steam boiler comprises at least two or more containers for the solar heating of a medium such as air. An exterior side of an exemplary boiler structure that is exposed to incident solar radiation is usually either coated with a blackened heat absorbing material or is covered with absorber plates as "fins". These absorber plates are normally made of metals such as copper or aluminum and are usually painted with selective coatings that absorb and retain heat better than ordinary black paint.

Metallic nanoparticles exhibit a very strong UV-VIS absorption band not present in the corresponding bulk spectrum. This absorption is due to the collective excitation of conduction electrons when particle sizes are smaller than the mean free path of carriers in these materials, an effect known as a localized surface plasmon resonance (LSPR). Subsequent non-radiative relaxation causes excess energy to be converted into heat. Metallic nanoparticles have therefore attracted great interest because of these unusual chemical and physical properties, which make them suitable for various applications such as catalysis, electronics, optics, and biotechnology. From this standpoint, the ability to tune the optical and electrical properties of metal nanostructures by gradually controlling their size and shape makes them unique systems.

In the practice of the present invention, one or more layers of metal nanoparticles are adsorbed onto thermally conductive graphene sheets and incorporated into the design of the solar stills and/or other apparatuses of the invention. The graphene-metal nanocomposites absorb sunlight with very high efficiency. When applied within the context of e.g. a solar steam boiler system, graphene sheets coated with metal nanoparticles increase the boiler's overall efficiency and ultimately produce steam at temperatures over 260° C. Incorporation of the graphene sheets may be accomplished by any of several methods, e.g. by attaching them to the photoabsorbing surface of the apparatus e.g. using a suitable adhesive; or by "painting", spraying or otherwise coating a liquid solution or dispersion of the graphene sheets onto a suitable surface (e.g. a photoabsorbing surface, the "fins" of a still, etc.); by incorporating the graphene sheets into a photoabsorbing material when it is manufactured, by adding particulate material directly to the water that is to be heated, etc.

Preliminary results have confirmed that this is the case.

Example 6. Solar Thermal Desalination

The general principle of solar desalination is based on the fact that glass and other like materials transmit incident short-wave solar radiation. In one embodiment of a solar-powered desalination apparatus, this visible radiation is directed so as to pass through a glass cover and into a container of sea water, and the incident radiation heats the sea water. Wavelengths re-radiated from the surface of the heated water have infrared frequencies, and very little of the infrared energy is transmitted back through the glass. As a consequence, this infrared energy is trapped and heats the sea water even further. This style of desalination system is generally suitable for small production rates, the still's output rate per unit area being relatively small. For example, a prior art well-designed unit having a thermal efficiency of about 50% can produce ~4.5 L/m$^2$/day. Furthermore, the equipment is both simple to construct and operate with little or no electrical needs. This lends itself to use in remote areas. However, for large capacity plants very large tracts of land are needed in order to make the process worthwhile since capital, land and civil engineering costs are inevitably high.

Figure 21:
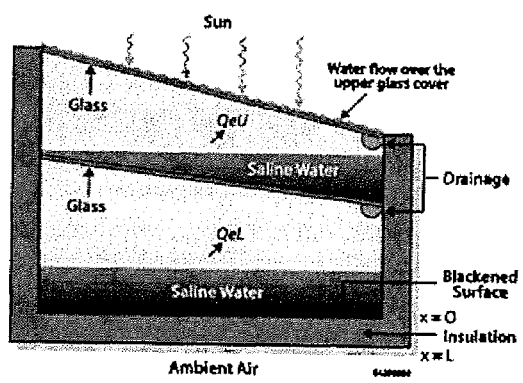
FIG. 21. Schematic of a simple solar still.

A schematic of an exemplary solar still is depicted in FIG. 21.

Nanomaterials that can be used in water purification and desalination processes include metal and metal oxide nanoparticles as well as graphene and carbon nanotubes. A methodology which combines solar desalination and nanotechnology has been developed in our laboratory. This approach is based on producing low cost graphene/gold/silver nanoparticle composites for water desalination. The resulting structures absorb light strongly and convert excess energy into heat in an efficient manner. These new composite materials are added to sea water to dramatically enhance the rate of water evaporation upon exposure to sunlight. For example, using the technology provided herein, production rates of ~10 or more (e.g. 20-100) L/m$^2$/day are attained.

The materials may be added to the sea water as particles, or the container that contains the sea water may be coated with the materials, or panels or sheets of the materials may be placed in juxtaposition to the sea water and in a manner that exposes the materials to incident sunlight, or in any other manner that provides efficient exposure of the materials to the sunlight, and transmission of the heat that is generated into the seawater. Sufficient heat is produced to cause evaporation of the sea water, and production of water vapor, which then is condensed to fresh water.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A method of producing fresh water by heating sea water via photothermal energy conversion, comprising the steps of
exposing at least one photothermally active material that is in contact with the sea water to a source of one or more of ultraviolet (UV), visible (VIS), or infrared (IR) radiant energy under conditions sufficient to produce heat from said photothermally active material, thereby causing evaporation of water vapor from the sea water, and condensing the water vapor to produce fresh water, wherein said photothermally active material is reduced graphene oxide comprising metal nanocrystals or semiconductor nanocrystals.

2. The method of claim 1, wherein said source of one or more of ultraviolet (UV), visible (VIS), or infrared (IR) light energy is sunlight.

3. The method of claim 1, wherein said source of one or more of ultraviolet (UV), visible (VIS), or infrared (IR) light energy is a laser.

4. The method of claim 1, wherein said source of one or more of ultraviolet (UV), visible (VIS), or infrared (IR) radiant energy is natural sunlight and wherein during said step of exposing, said at least one photothermally active material is positioned so that incident natural sunlight impinges on said at least one photothermally active material.

5. The method of claim 1, wherein the metal nanocrystals are selected from the group consisting of Au, Ag, Pd, Co, Pd, Co, Au, Ag, Cu, Pt, Ni, Fe, Mn, Cr, V, Ti, Sc, Ce, Pr, Nd, Sm, Gd, Ho, Er, Yb, Al, Ga, Sn, Pb, In, Mg, Ca, Sr, Na, K, Rb, and Cs nanocrystals, and combinations thereof.

6. The method of claim 1, wherein the semiconductor nanocrystals are selected from the group consisting of Si, Ge, CdSe, CdS, CdTe, ZnO, ZnS, and ZnSe nanocrystals.

7. The method of claim 1, wherein the method further comprises, after the step of exposing, a step of cooling the seawater, and wherein the steps of exposing and cooling are performed repeatedly.

8. The method of claim 7, wherein the step of cooling is performed by turning off or reducing exposure to the radiant energy.

9. The method of claim 1, wherein the at least one photothermally active material is i) dispersed in the sea water or ii) coated onto a support or substrate submerged in the sea water.

10. An apparatus for desalinating sea water, comprising
a container for containing at least one photothermally active material, said container permitting exposure of said at least one photothermally active material to a source of one or more of ultraviolet (UV), visible (VIS), or infrared (IR) light energy,
wherein said photothermally active material is reduced graphene oxide which comprises nanocrystals of a metal or nanocrystals of a semiconductor;
a container for containing sea water;
a condenser for condensing water vapor; and
a receptacle for receiving condensed water vapor.

11. The apparatus of claim 10, wherein said container for containing at least one photothermally active material and said container for containing sea water are the same container.

12. The apparatus of claim 10, wherein said source of one or more of ultraviolet (UV), visible (VIS), or infrared (IR) radiant energy is natural sunlight and said container is configured so that incident natural sunlight impinges on said at least one photothermally active material.

13. The apparatus of claim 10, wherein the metal nanocrystals are selected from the group consisting of Au, Ag, Pd, Co, Pd, Co, Au, Ag, Cu, Pt, Ni, Fe, Mn, Cr, V, Ti, Sc, Ce, Pr, Nd, Sm, Gd, Ho Er, Yb, Al, Ga, Sn, Pb, In, Mg, Ca, Sr, Na, K, Rb, and Cs nanocrystals, and combinations thereof.

14. The apparatus of claim 10 wherein the semiconductor nanocrystals are selected from the group consisting of Si, Ge, CdSe, CdS, CdTe, ZnO, ZnS, and ZnSe nanocrystals.

15. A method of heating water, comprising the steps of
producing heat by exposing at least one photothermally active material to a source of one or more of ultraviolet (UV), visible (VIS), or infrared (IR) radiant energy, wherein the at least one photothermally active material is reduced graphene oxide comprising metal nanocrystals or semiconductor nanocrystals, and
utilizing the heat to heat the water.

16. The method of claim 15, wherein the water that is heated is for domestic use.

17. The method of claim 15, wherein the source of one or more of ultraviolet (UV), visible (VIS), or infrared (IR) light energy is sunlight.

18. The method of claim 15, wherein the source of one or more of ultraviolet (UV), visible (VIS), or infrared (IR) light energy is a laser.

19. The method of claim 15, wherein the metal nanocrystals are selected from the group consisting of Au, Ag, Pd, Co, Pd, Co, Au, Ag, Cu, Pt, Ni, Fe, Mn, Cr, V, Ti, Sc, Ce, Pr, Nd, Sm, Gd, Ho, Er, Yb, Al, Ga, Sn, Pb, In, Mg, Ca, Sr, Na, K, Rb, and Cs nanocrystals, and combinations thereof.

20. The method of claim 15, wherein the semiconductor nanocrystals are selected from the group consisting of Si, Ge, CdSe, CdS, CdTe, ZnO, ZnS, and ZnSe nanocrystals.

21. An apparatus for heating water, comprising
a container for containing the water, and
at least one photothermally active material positioned on or incorporated into the container so as to permit exposure of said at least one photothermally active material to a source of one or more of ultraviolet (UV), visible (VIS), or infrared (IR) light energy,
wherein said photothermally active material is reduced graphene oxide which comprises nanocrystals of a metal or nanocrystals of a semiconductor;
and wherein the container is configured so that heat, generated when the at least one photothermally active material is exposed to the source of one or more of ultraviolet (UV), visible (VIS), or infrared (IR) light energy, heats the water contained in the container.

22. The apparatus of claim 21, wherein the at least one photothermally active material is attached to, painted on or coated on the container.

* * * * *